(12) United States Patent
Park et al.

(10) Patent No.: US 9,512,315 B2
(45) Date of Patent: Dec. 6, 2016

(54) QUENCHING DYE FOR LABELING BIOMOLECULES AND METHOD FOR PREPARING THE SAME

(71) Applicant: DKC CORPORATION, Incheon (KR)

(72) Inventors: Jin Woo Park, Incheon (KR); Kiwon Kim, Incheon (KR)

(73) Assignee: DKC Corporation, Incheon (KR)

( * ) Notice: Subject to any disclaimer, the term of this patent is extended or adjusted under 35 U.S.C. 154(b) by 0 days.

(21) Appl. No.: 15/033,478

(22) PCT Filed: Oct. 31, 2013

(86) PCT No.: PCT/KR2013/009791
§ 371 (c)(1),
(2) Date: Apr. 29, 2016

(87) PCT Pub. No.: WO2015/064787
PCT Pub. Date: May 7, 2015

(65) Prior Publication Data
US 2016/0266130 A1 Sep. 15, 2016

(51) Int. Cl.
*C09B 62/45* (2006.01)
*G01N 33/58* (2006.01)

(52) U.S. Cl.
CPC ............. *C09B 62/45* (2013.01); *G01N 33/582* (2013.01)

(58) Field of Classification Search
CPC .............................. C09B 62/45; G01N 33/582
See application file for complete search history.

(56) References Cited

U.S. PATENT DOCUMENTS

| | | | |
|---|---|---|---|
| 3,391,134 A * | 7/1968 | Kuhne | C09B 62/006 534/591 |
| 4,394,310 A | 7/1983 | Fuchs et al. | |
| 5,536,277 A | 7/1996 | Shimode et al. | |
| 6,696,553 B1 | 2/2004 | Körte | |
| 2004/0110308 A1 | 6/2004 | Laikhter et al. | |

* cited by examiner

*Primary Examiner* — Joseph Kosack
(74) *Attorney, Agent, or Firm* — Duane Morris LLP; J. Rodman Steele, Jr.; Gregory M. Lefkowitz

(57) ABSTRACT

The present disclosure provides a quenching dye with an anthraquinone structure, which has a broad and high absorption spectrum in the visible and near-infrared wavelength regions and exhibits high stability and superior solubility in aqueous conditions. A quenching dye composition containing the anthraquinone compound according to the present disclosure as an active ingredient can be widely used in the field of optical molecular imaging to observe the movement of a biomolecule because it can easily label a biomolecule manipulated in an aqueous buffer.

12 Claims, 2 Drawing Sheets

QUENCHING DYE FOR LABELING BIOMOLECULES AND METHOD FOR PREPARING THE SAME

CROSS-REFERENCE TO RELATED APPLICATIONS

This application is a §371 national stage entry of International Application No. PCT/KR2013/009791, filed Oct. 31, 2013, the entire contents of which are incorporated herein by reference.

TECHNICAL FIELD

The present disclosure relates to a quenching dye capable of labeling various biomolecules, more particularly a quenching dye which exhibits strong absorption intensity in the visible and near-infrared wavelength regions and exhibits superior solubility and high stability in aqueous condition, thus being useful in labeling and imaging of biomolecules, and a method for preparing the same.

BACKGROUND ART

A quencher refers to a molecule capable of quenching the fluorescence from a fluorescent molecule. Usually, a dye capable of absorbing light is used as the quencher. It is known that the quenching occurs via such mechanisms as fluorescence resonance energy transfer (FRET), photo-induced electron transfer and dye aggregation such as H-dimerization.

When selecting a quenching dye for controlling or quenching the fluorescence of a fluorescent dye. It is of the most importance whether the absorption wavelength range of the quenching dye covers (overlaps with) the fluorescence wavelength range of the fluorescent dye. In addition, the distance between the fluorescent dye and the quenching dye is also important. For example, the number of nucleotides in DNAs and the number of amino acids in peptides/protein need to be considered. Often, the length of a linker labeled with the fluorescent and quenching dyes is controlled to achieve a higher quenching effect.

In biological fields, commercially available quenching dye-fluorescent dye pairs are used. For example, combinations of FITC (ex/em, 490/520)-BHQ-1, TRITC (ex/em, 547/572)-BHQ-2, Cy5.5 (ex/em, 670/690)-BHQ-3 etc. are used. In FRET, a combination of fluorescent-fluorescent dyes is also used frequently. These combinations of fluorescent-quenching or fluorescent-florescent dyes may act like on/off switches of fluorescence because the original fluorescence is restored or reinforced as the distance between them increases or they are separated in a biomolecule. Due to these characteristics, they are frequently used when designing biosensors, molecular probes, etc. that can respond sensitively to biomarkers such as particular proteins, enzymes, etc.

Any dye that covers the maximum absorption wavelength or the entire fluorescence spectrum of a fluorescent dye to be used can be used as a quenching dye. However, the inventors of the present disclosure have noted dyes for dyeing fibers, which are known to strongly absorb light of a particular wavelength and exhibit vivid colors. As the dyes for dyeing fibers, azo dyes or anthraquinone dyes are used the most widely used industrially. The BHQ quenching dye frequently used in the biological field is also an azo chromophore dye belonging to the class of direct dyes. The anthraquinone dyes are usually used to exhibit blue and green colors and are known to have absorption wavelengths of 550 nm or higher.

The fluorescent or quenching dyes used in the biological field are limited to those approved by the FDA, such as indocyanine green or methylene blue. In general, a functional group that can react with the substituent of a biomolecule is introduced into the dye. Several functional groups are known and have been confirmed by many researchers in terms of substituent selectivity, reaction rate, yield, reproducibility, stability, etc. Recently, the functional groups introduced into dyes for researches or commercial purposes are restricted to a few. For example, succinimidyl ester and isothiocyanate are the most frequently used as a functional group for binding with the amine group of a protein molecule, maleimide is the most frequently used as a functional group for binding with the thiol group of a protein molecule, and dichlorotriazine is mainly selected as a functional group for binding with the hydroxyl group of a protein molecule. However, these functional groups are difficult to maintain reaction or storage stability for a long time in aqueous conditions. It is known that quenching dyes maintain optical properties almost constantly within the range of a few nanometers if there is no structural change in the chromophore.

DISCLOSURE

Technical Problem

The present disclosure is directed to providing a novel quenching dye having an anthraquinone structure, which can be widely used in the field of optical molecular imaging to observe the movement of a biomolecule, and a method for preparing the same.

Technical Solution

In an aspect, the present disclosure provides an anthraquinone compound represented by [Chemical Formula 1] and a method for preparing the same.

[Chemical Formula 1]

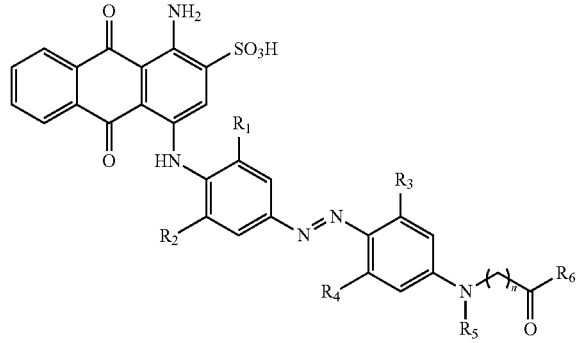

In [Chemical Formula 1],
each of $R_1$, $R_2$, $R_3$ and $R_4$, which are identical to or different from each other, is independently selected from hydrogen, a hydroxyl group, an amine group, a nitro group, a $C_1$-$C_6$ alkyl group, a $C_7$-$C_{10}$ alkyl group, a $C_1$-$C_6$ alkoxy group, a sulfonic acid group and a sulfonate group,
$R_5$ is selected from a $C_1$-$C_6$ alkyl group and a $C_7$-$C_{10}$ alkyl group, $R_6$ is selected from a hydroxyl group, a hydrazinyl group, $NH(CH_2)_pNH_2$, a N-hydroxysuccinimide group, $NH-(CH_2)_q-N(CO)_2C_2H_2$, a 2,4-dihalo-6-hydrazino-1,3,5-triazine group and $NH-A-SO_2CH=CH_2$, A is selected from $(CH_2)_m$, para-$(C_6H_4)$ and meta-$(C_6H_4)$, each of m, p and q, which are identical to or different from each other, is independently an integer from 1 to 10, and n is an integer from 1 to 23.

In another aspect, the present disclosure provides a quenching dye composition containing the anthraquinone compound represented by [Chemical Formula 1] as an active ingredient.

Advantageous Effects

An anthraquinone compound according to the present disclosure has a broad and high absorption spectrum in the visible and near-infrared wavelength regions so that all the fluorescence wavelength ranges of commercially available visible and near-infrared dyes can be covered and also has high stability and superior solubility in aqueous conditions. Also, because it can easily label a biomolecule manipulated in an aqueous buffer, it can be widely used in the field of optical molecular imaging to observe the movement of a biomolecule.

BEST MODE

Figure 1:
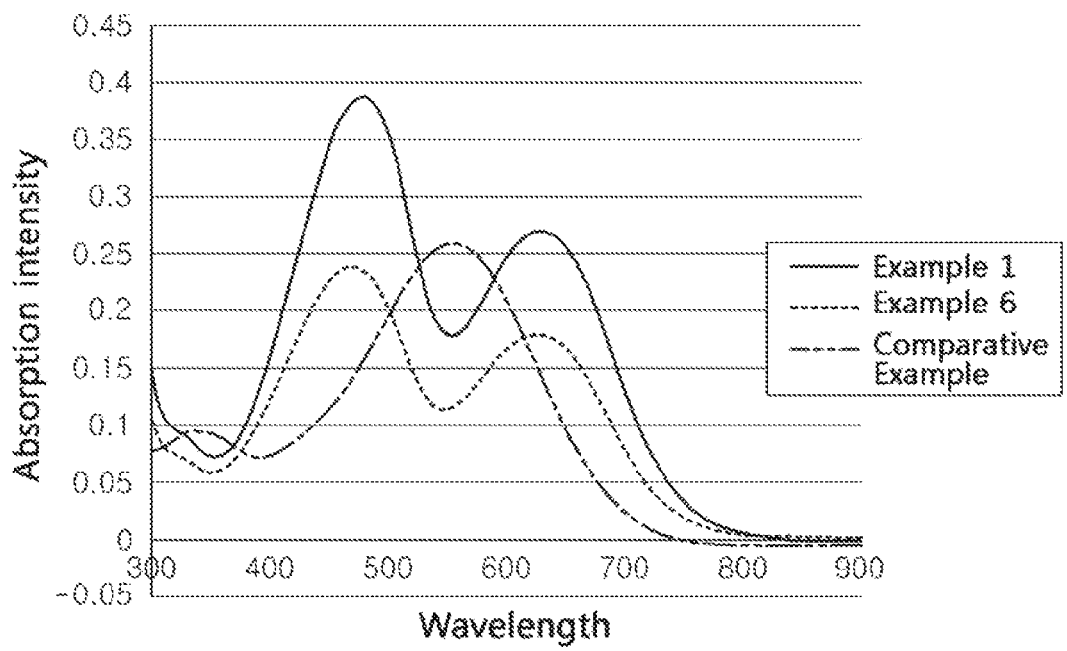
FIG. 1 shows the absorption spectra of compounds according to an exemplary embodiment of the present disclosure and a comparative example.

The present disclosure relates to a quenching dye compound that can be used in combination with fluorescent dyes widely used for labeling of biomolecules. In particular, the inventors of the present disclosure have made consistent efforts to prepare a compound which has a broad absorption spectrum so as to cover the visible and near-infrared wavelength regions and also has high stability and superior solubility in aqueous conditions so that it can easily label a biomolecule manipulated in an aqueous buffer. As a result, they have developed an anthraquinone compound according to the present disclosure.

Hereinafter, the present disclosure is described in more detail.

The present disclosure provides an anthraquinone compound represented by [Chemical Formula 1]:

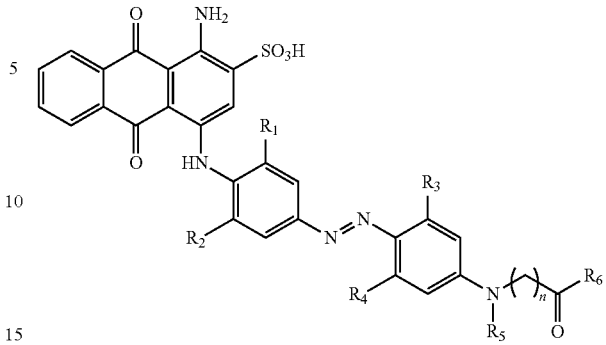

[Chemical Formula 1]

wherein each of $R_1$, $R_2$, $R_3$ and $R_4$, which are identical to or different from each other, is independently selected from hydrogen, a hydroxyl group, an amine group, a nitro group, a $C_1$-$C_6$ alkyl group; a $C_7$-$C_{10}$ alkyl group, a $C_1$-$C_6$ alkoxy group, a sulfonic acid group and a sulfonate group, $R_5$ is selected from a alkyl group and a $C_7$-$C_{10}$ alkyl group, $R_6$ is selected from a hydroxyl group, a hydrazinyl group, $NH(CH_2)_pNH_2$, a N-hydroxysuccinimide group, $NH-(CH_2)_q-N(CO)_2C_2H_2$, a 2,4-dihalo-6-hydrazino-1,3,5-triazine group and $NH-A-SO_2CH=CH_2$, A is selected from $(CH_2)_m$, para-$(C_6H_4)$ and meta-$(C_6H_4)$, each of m, p and q, which are identical to or different from each other, is independently an integer from 1 to 10, and n is an integer from 1 to 23.

The $NH-(CH_2)_q-N(CO)_2C_2H_2$ in $R_6$ means.

In the present disclosure, the compound of [Chemical Formula 1] may be a compound of [Chemical Formula 4] or [Chemical Formula 5].

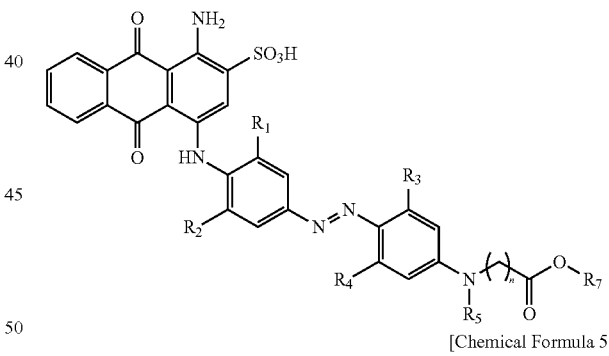

[Chemical Formula 4]

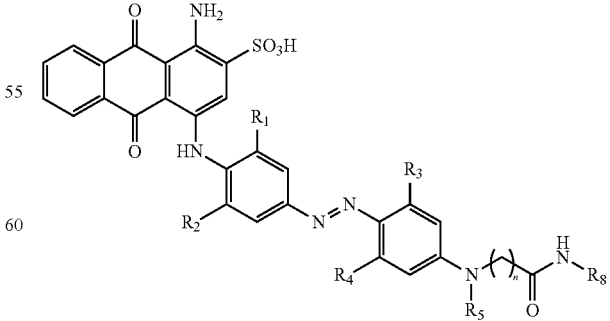

[Chemical Formula 5]

In [Chemical Formula 4] or [Chemical Formula 5], each of $R_1$, $R_2$, $R_3$, $R_4$, $R_5$, A, m and n is the same as defined in [Chemical Formula 1], $R_7$ is hydrogen or a succinimide group, and $R_8$ is selected from an amine group, a $C_1$-$C_{10}$ alkylamine group, a $C_1$-$C_{10}$ alkylmaleimidyl group, a 2,4-dihalo-6-amino-1,3,5-triazine group and A—$SO_2CH=CH_2$.

Specifically, the compound of [Chemical Formula 1] may be selected from a group of compounds represented by [Chemical Formula 6] through [Chemical Formula 19], although not being limited thereto.

[Chemical Formula 6]

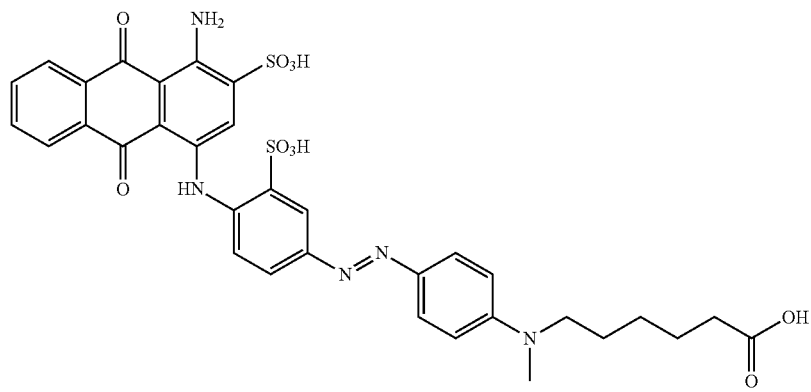

[Chemical Formula 7]

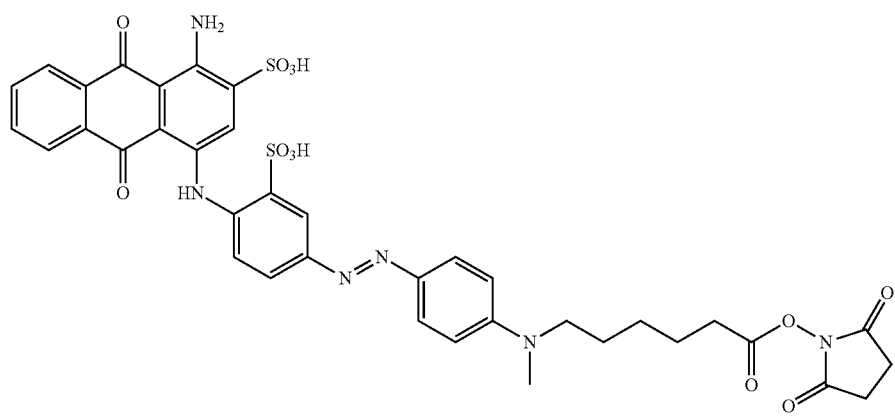

[Chemical Formula 8]

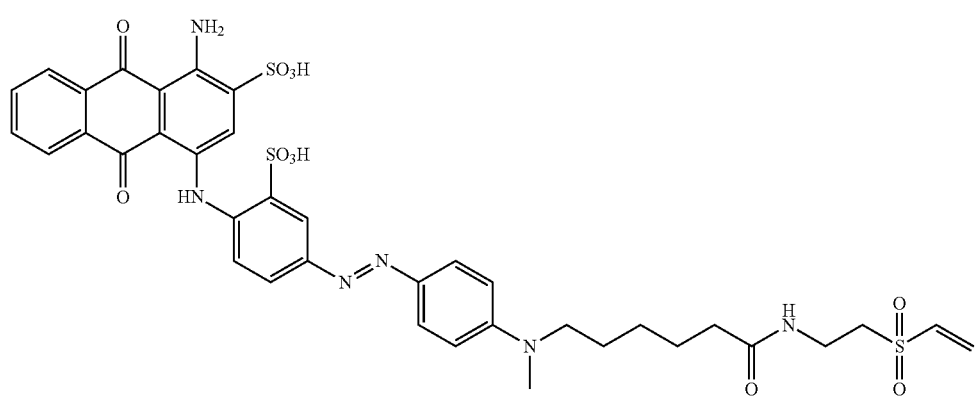

-continued
[Chemical Formula 9]
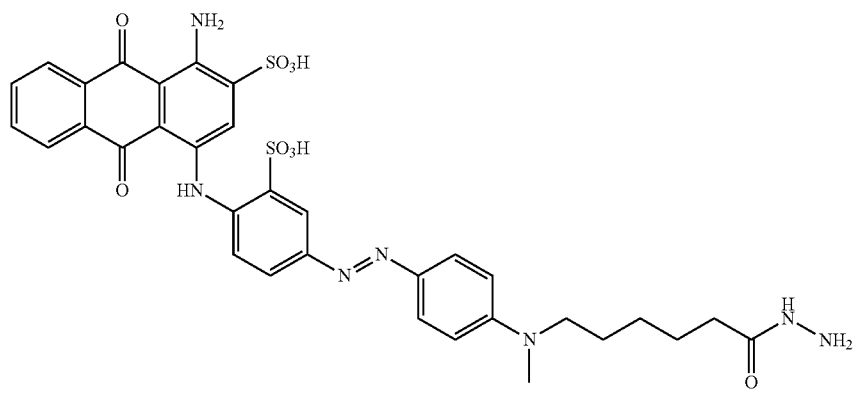
[Chemical Formula 10]
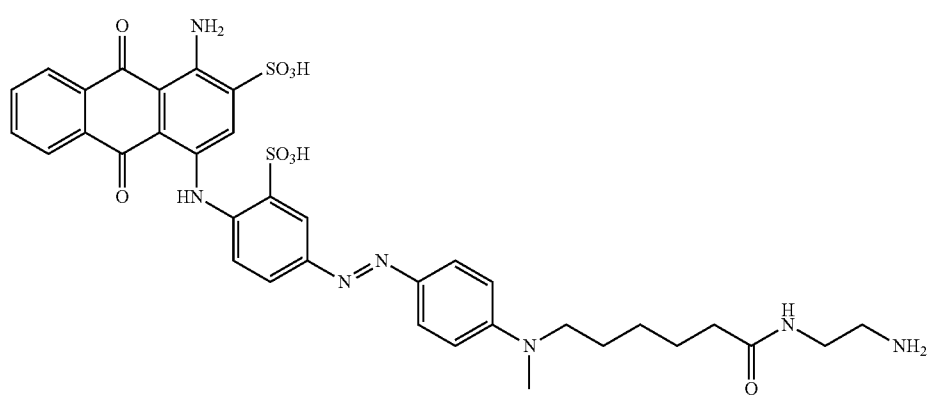
[Chemical Formula 11]
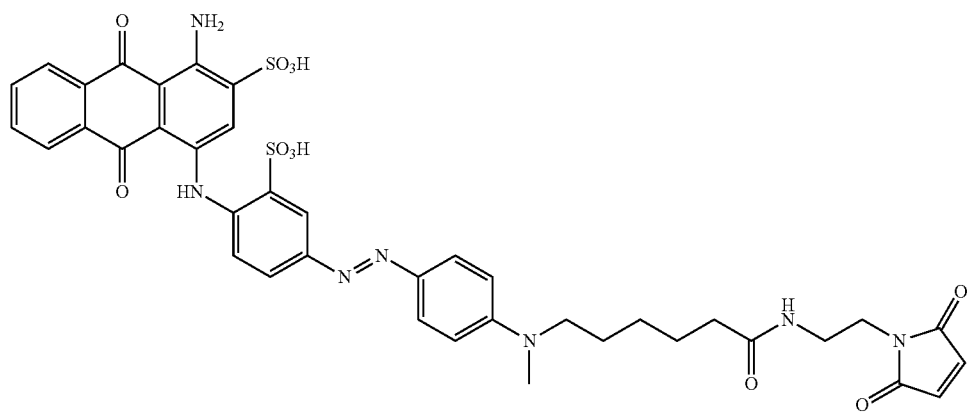
[Chemical Formula 12]
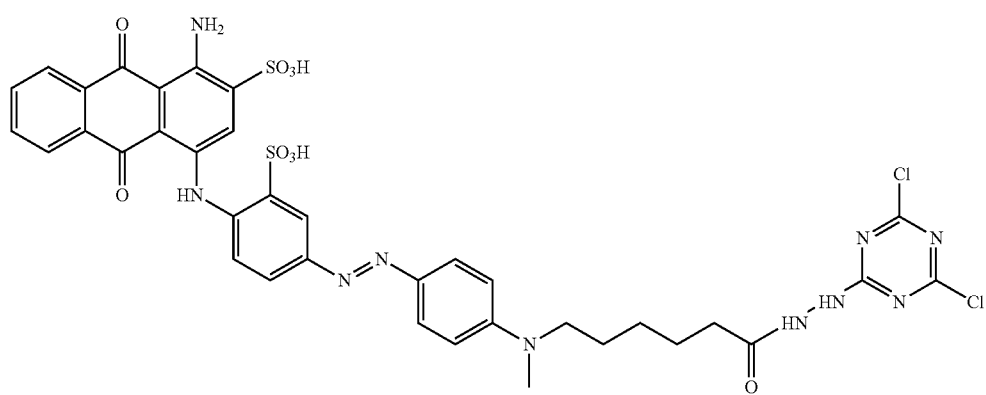

[Chemical Formula 13]
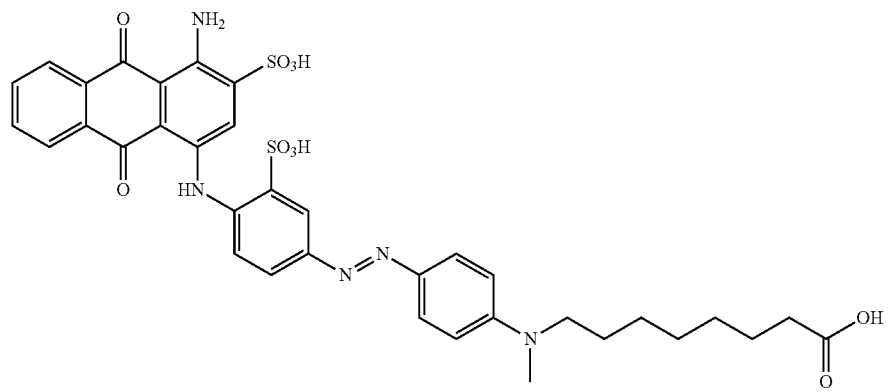
[Chemical Formula 14]
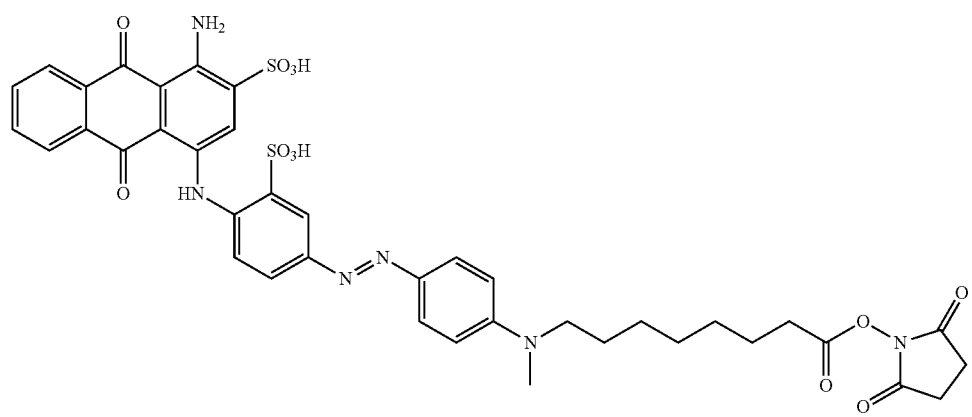
[Chemical Formula 15]
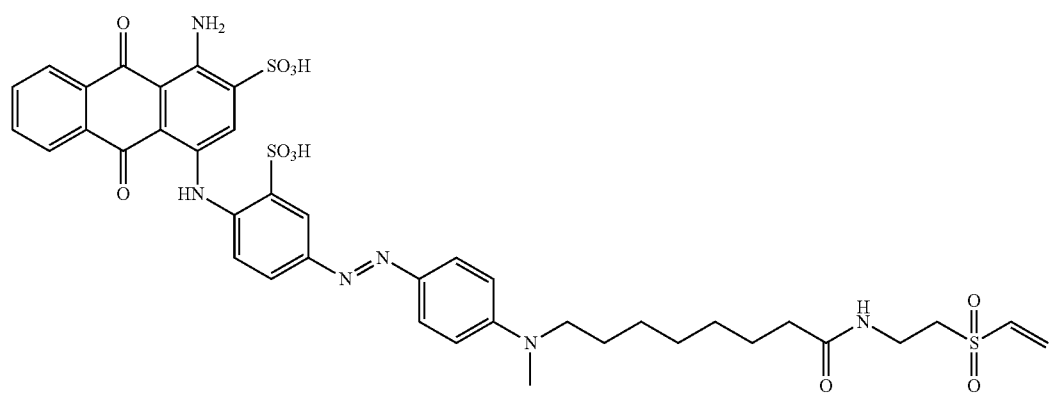
[Chemical Formula 16]
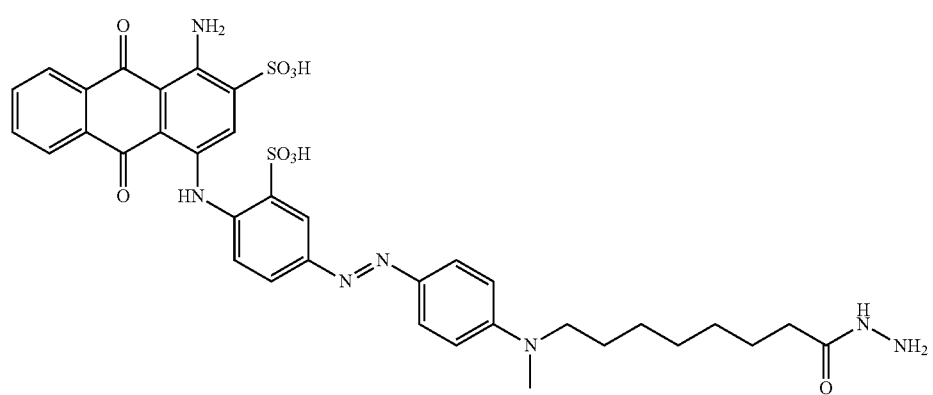

[Chemical Formula 17]

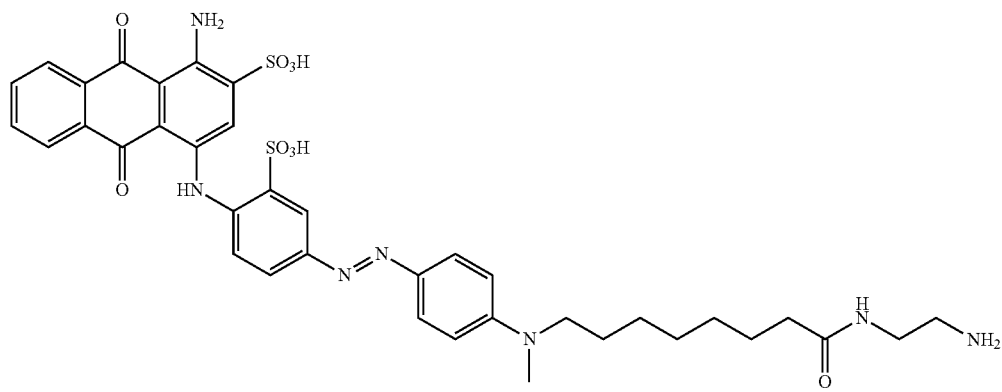

[Chemical Formula 18]

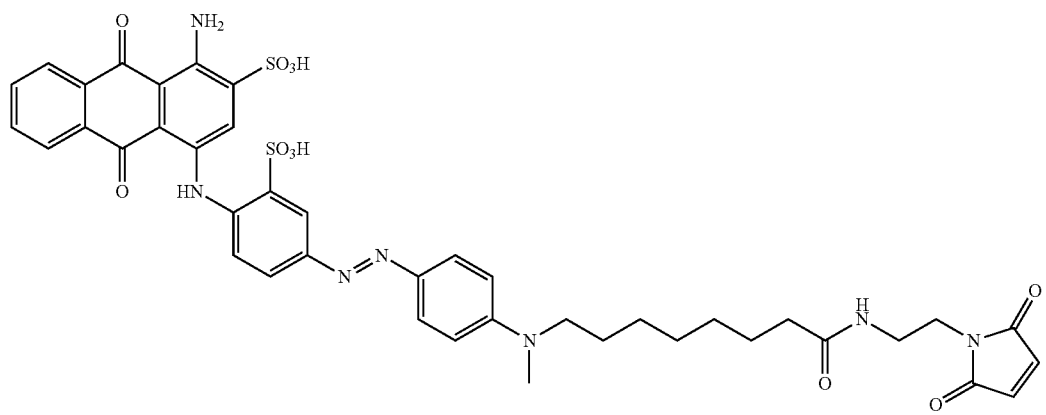

[Chemical Formula 19]

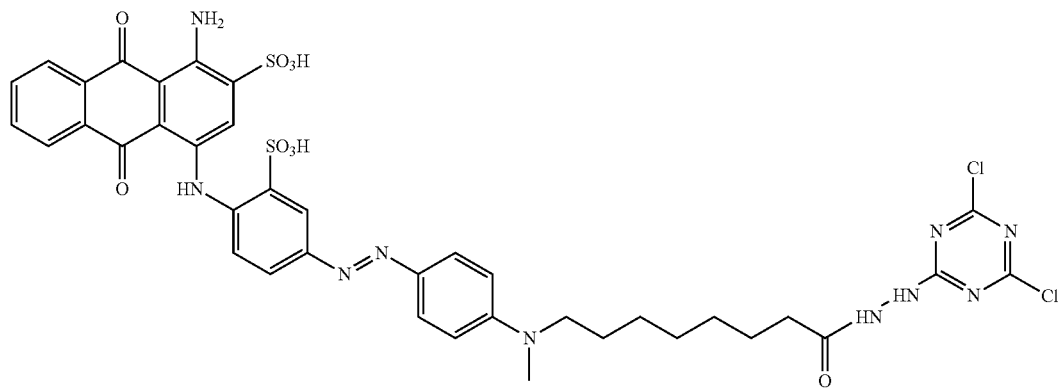

The anthraquinone compound represented by [Chemical Formula 1] according to the present disclosure may absorb light with a wavelength of 300-900 nm in the visible and near-infrared fluorescence regions.

The anthraquinone compound represented by [Chemical Formula 1] according to the present disclosure may label a biomolecule containing one or more of an amine group, a hydroxyl group or a thio group.

The biomolecule may be one selected from a group consisting of a protein, a peptide, a carbohydrate, a sugar, a fat, an antibody, a proteoglycan, a glycoprotein and a siRNA.

The biomolecule may be a biomolecule which has not been modified physically or chemically. However, it may also be a biomolecule which has been modified physically or chemically. The biomolecule which has been modified physically or chemically may be, for example, a biomolecule labeled with a fluorescent compound.

The anthraquinone compound represented by [Chemical Formula 1] according to the present disclosure may be used in the study of a biomolecule by labeling the biomolecule with the anthraquinone compound. Also it may be used to control or quench the fluorescence of a biomolecule labeled with a fluorescent compound by labeling with the anthraquinone compound.

A biomolecule may be labeled with the anthraquinone compound represented by [Chemical Formula 1] by reacting the compound of [Chemical Formula 1] with the biomolecule at pH 5-12 using a buffer selected from a group consisting of a phosphate buffer, a carbonate buffer and a Tris buffer, an organic solvent selected from a group consisting of dimethyl sulfoxide, dimethylformamide, methanol, ethanol and acetonitrile or water as a solvent. The reaction may be performed at 20-80° C. for 30 minutes to 48 hours.

Because biomolecules are provided as dissolved in specific buffers and specific buffers or pH conditions are required to ensure the stability of the biomolecules in most cases, it is not easy to control the many parameters. Because the compound of [Chemical Formula 1] according to the present disclosure absorbs light in the visible and near-infrared wavelength regions by easily reacting with biomolecules in various buffers under various reaction temperature and pH conditions, it is suitable for labeling biomolecules.

The present disclosure provides a method for preparing the anthraquinone compound represented by [Chemical Formula 1].

The anthraquinone compound represented by [Chemical Formula 1] according to the present disclosure may be prepared by a method including: a step of preparing a compound represented by [Chemical Formula 2] into a diazonium salt; and a step of reacting the diazonium salt with a compound of [Chemical Formula 3].

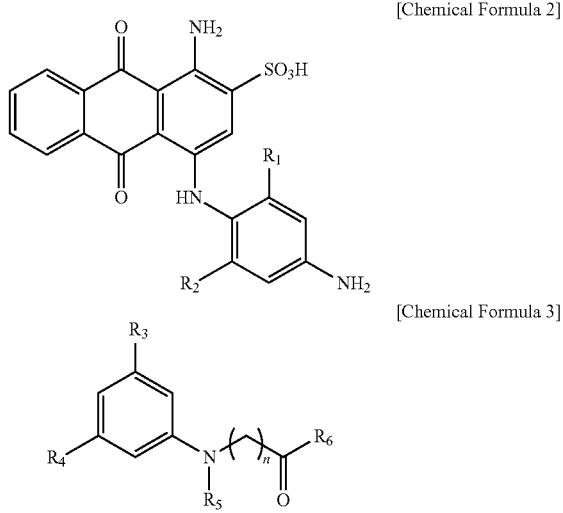

[Chemical Formula 2]

[Chemical Formula 3]

In [Chemical Formula 2] or [Chemical Formula 3], each of $R_1$, $R_2$, $R_3$, $R_4$, $R_5$, $R_6$ and n is the same as defined in [Chemical Formula 1].

The diazonium salt may be prepared by any common method without limitation. For example, it may be prepared by preparing a hydrochloride by adding strong hydrochloric acid to the compound of [Chemical Formula 2] and then adding sodium nitrite to the hydrochloride (hereinafter, forward diazo method). Also, it may be prepared by adding excess sodium nitrite to the compound of [Chemical Formula 2] and then adding excess hydrochloric acid (hereinafter, reverse diazo method).

To describe the method for preparing the compound of [Chemical Formula 1] in detail, the compound of [Chemical Formula 2] may be dissolved or prepared into a hydrochloride by adding 3-50 equivalents of strong hydrochloric acid to 1 equivalent of the compound in an aqueous solution. Then, a diazonium salt may be formed by adding 1-10 equivalents of sodium nitrite at −20 to 5° C. under an acidic condition of pH 1-5.5. Then, the compound of [Chemical Formula 3] may be reacted with the diazonium salt after dissolving in an aqueous solution of pH 6.5-10 (neutral to alkaline) or an organic solvent.

As another method, it may be prepared by dissolving the compound of [Chemical Formula 2] in an organic solvent and cooling to −20 to 5° C., adding 1-10 equivalents of sodium nitrite to 1 equivalent of the compound of [Chemical Formula 2] and then adding 3-50 equivalents of strong hydrochloric acid.

The organic solvent may be one or more selected from a group consisting of 1,2-dichloroethane, dichloromethane, chloroform, acetonitrile, dioxane, tetrahydrofuran, N,N-dimethylformamide, methanol and ethanol.

A suitable pH during the coupling of the compound of [Chemical Formula 2] and the compound of [Chemical Formula 3] may vary depending on the functional groups $R_1$, $R_2$, $R_3$, $R_4$, $R_5$ and $R_6$. In general, the reaction may be performed at weakly acidic, neutral or alkaline pH of pH 5.5-10 for 1-24 hours, although not being limited thereto. The reaction is shown in Scheme 1.

[Scheme 1]

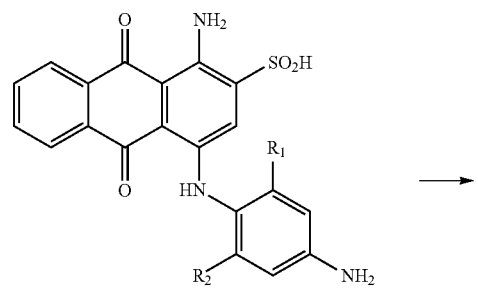

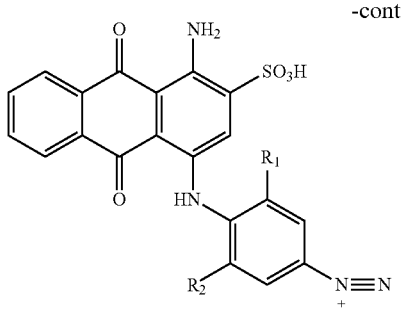
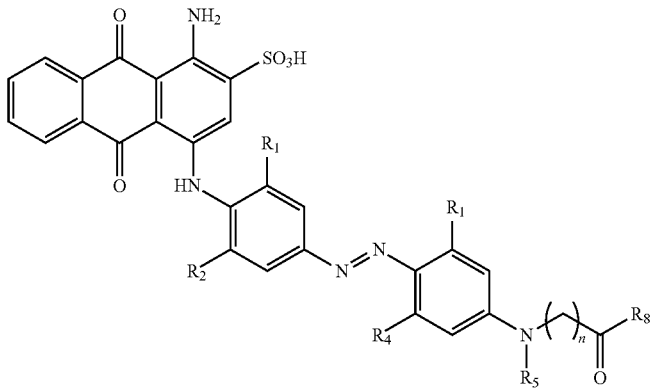

The step of preparing the compound of [Chemical Formula 1] by reacting the compound of [Chemical Formula 2] with the compound of [Chemical Formula 3] may be performed via a one step. However, it may also be performed via two or more steps.

For example, [Chemical Formula 1] may be [Chemical Formula 4] or [Chemical Formula 5].

[Chemical Formula 4]

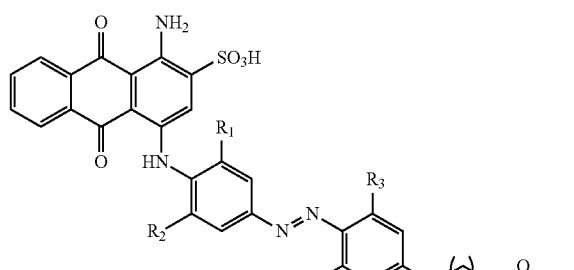

[Chemical Formula 5]

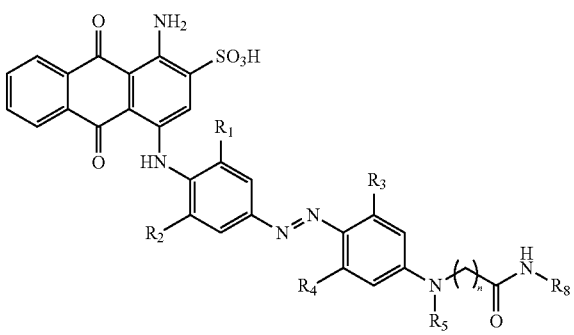

In [Chemical Formula 4] or [Chemical Formula 5], each of $R_1$, $R_2$, $R_3$, $R_4$, $R_5$ and n is the same as defined in [Chemical Formula 1], $R_7$ is hydrogen or a succinimide group, $R_8$ is selected from an amine group, a $C_1$-$C_{10}$ alkylamine group, a $C_1$-$C_{10}$ alkylmaleimidyl group, a 2,4-dihalo-6-amino-1,3,5-triazine group and A—$SO_2CH$=$CH_2$, A is selected from $(CH_2)_m$, para-$(C_6H_4)$ and meta-$(C_6H_4)$, and m is an integer from 1 to 10.

The compound wherein $R_7$ in [Chemical Formula 4] is a succinimide group may be prepared by reacting the compound wherein $R_7$ in [Chemical Formula 4] is hydrogen with N,N'-disuccinimidyl carbonate (DSC) or O-(benzotriazol-1-yl)-N,N,N',N'-tetramethyluroniumhexafluorophosphate (HBTU) in an organic solvent.

The compound wherein $R_8$ in [Chemical Formula 5] is A—$SO_2CH$=$CH_2$ may be prepared by reacting the compound wherein $R_7$ in [Chemical Formula 4] is a succinimide group with a vinylsulfonylalkylamine ($NH_2$—A—$SO_2CH$=$CH_2$. A is the same as defined in [Chemical Formula 1]) or a vinylsulfonylalkylamine hydrochloride in an organic solvent.

The compound wherein $R_8$ in [Chemical Formula 5] is an amine group, a $C_1$-$C_{10}$ alkylamine group, A—$SO_2CH$=$CH_2$, a $C_1$-$C_{10}$ alkylmaleimidyl group or a 2,4-dihalo-6-amino-1,3,5-triazine group may be prepared by reacting the compound of [Chemical Formula 4] with an amine compound or an amine compound protected with a protecting group.

The amine compound may be hydrazine, an alkyldiamine ($NH_2(CH_2)_pNH_2$, p is an integer from 1 to 10), a vinylsulfonylalkylamine ($NH_2$—A—$SO_2CH$=$CH_2$, A is the same as defined in [Chemical Formula 1]), a maleimidylalkylamine ($NH_2(CH_2)_q$—$N(CO)_2C_2H_2$, q is an integer from 1 to 10) or 2,4-dihalo-6-hydrazinyl-1,3,5-triazine.

Specific examples of the amine compound include hydrazine, ethylenediamine, N-(2-aminoethyl)maleimide and 4,6-dichloro-2-hydrazinyl-1,3,5-triazine, and the amine compound protected with a protecting group may be tert-butyl carbazate, although not being limited thereto.

The compound of [Chemical Formula 4] may be a compound wherein $R_7$ in [Chemical Formula 4] is hydrogen or a compound wherein $R_7$ is a succinimide group.

The organic solvents used in the reactions may be identical to or different from each other and may be independently one or more selected from a group consisting of 1,2-dichloroethane, dichloromethane, chloroform, acetonitrile, dioxane, tetrahydrofuran, N,N-dimethylformamide, methanol and ethanol.

The compound of [Chemical Formula 2] may be prepared by dispersing bromaminic acid in an aqueous solution using a dispersant such as Dywell and then performing condensation at 15-80° C. after adding a benzene derivative containing an amine group and a copper catalyst.

The present disclosure provides a quenching dye composition containing the anthraquinone compound represented by [Chemical Formula 1] as an active ingredient.

Because the anthraquinone compound of [Chemical Formula 1] according to the present disclosure can absorb light with a wavelength of 300-900 nm in the visible and near-infrared wavelength regions, the composition containing the same as an active ingredient may be effectively used to quench or restore the fluorescence of a biomolecule and thus can be usefully used in biomolecule imaging.

The present disclosure provides a method for labeling a biomolecule, including a step of binding the anthraquinone compound represented by [Chemical Formula 1] to a biomolecule.

The biomolecule may contain at least one functional group selected from an amine group, a hydroxyl group and a thiol group and the labeling may be achieved by binding the vinylsulfonyl group, amine group or halogen group present in the compound of [Chemical Formula 1] with the amine group, hydroxyl group or thiol group present in the biomolecule.

The biomolecule may be one or more selected from a group consisting of a protein, a peptide, a carbohydrate, a sugar, a fat, an antibody, a proteoglycan, a glycoprotein and a siRNA.

The biomolecule may be a biomolecule which has not been modified physically or chemically. However, it may also be a biomolecule which has been modified physically or chemically. The biomolecule which has been modified physically or chemically may be, for example, a biomolecule labeled with a fluorescent compound.

Specifically, the fluorescent compound may be a compound which fluoresces in the wavelength range of 300-900 nm.

The labeling may be performed by reacting the compound of [Chemical Formula 1] with the biomolecule at pH 5-12 using a buffer selected from a group consisting of a phosphate buffer, a carbonate buffer and a Iris buffer, an organic solvent selected from a group consisting of dimethyl sulfoxide, dimethylformamide, methanol, ethanol and acetonitrile or water as a solvent. The reaction may be performed at 20-80° C. for 30 minutes to 48 hours.

Because biomolecules are provided as dissolved in specific buffers and specific buffers or pH conditions are required to ensure the stability of the biomolecules in most cases, it is not easy to control the many parameters. Because the compound of [Chemical Formula 1] according to the present disclosure can be stored for a long time in aqueous conditions due to high stability and fluoresces by easily reacting with biomolecules in various buffers under various reaction temperature and pH conditions, it is suitable for labeling biomolecules.

Mode for Invention

Hereinafter, the present disclosure will be described in detail through examples. However, the following examples are for illustrative purposes only and the scope of the present disclosure is not limited by them.

The experimental apparatuses, analysis instruments and reagents used in the examples are described in the followings.

LC/MS was measured by ESI (electrospray ionization) using the LC/MSD SL of Agilent Technologies. The absorption spectrum and maximum absorption wavelength ($\lambda_{abs}$) of the synthesized dye were measured with Lambda 45 of PerkinElmer. The emission spectrum and maximum emission wavelength ($\lambda_{fl}$) were measured with LS-55 of PerkinElmer.

Form the normal phase, column chromatography for separation and purification of organic compounds was performed using the Merck's silica gel Kieselgel 60 (230-400 mesh) and thin-layer chromatography (TLC) was performed using a glass plate coated with the silica gel 60GF254 (0.25 mm, Merck). The identification of compounds on TLC was performed using 254-nm and 365-nm UV light. For the reverse phase, TLC was performed using a glass plate coated with the silica gel 60 RP-18 F254S (0.25 mm, Merck) and column chromatography was performed using the Buchi's MPLC (medium pressure liquid chromatography) instrument Fraction Collector R-660 coupled with the reverse-phase column LiChroprep RP-18 (40-63 μm, Merck).

Reagents were purchased mostly from Aldrich and TCI. Solvents requiring purification were purified according to known methods. Unless stated otherwise, all reactions were performed under nitrogen flow.

Preparation Examples

Preparation Example 1

Preparation of Compound of [Chemical Formula 2-1]

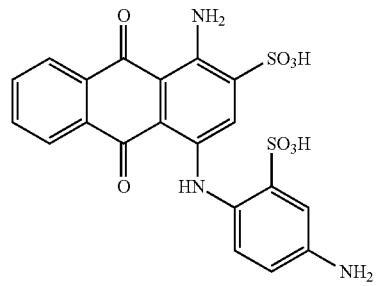 [SMILES: Nc1ccc(Nc2cc(S(=O)(=O)O)c(N)c3c2C(=O)c2ccccc2C3=O)c(S(=O)(=O)O)c1]

After dispersing 10 g of sodium bromaminate (24.7 mmol, 1 eq) in 100 mL of distilled water, 6.3 g of sodium carbonate and 1.3 g of sodium sulfite were added. After stirring at 35° C. for 30 minutes, 5.2 g of 2,5-diaminobenzenesulfonic acid (24.7 mmol, 1 eq) was added. After stirring further for 30 minutes, 0.1 g of copper chloride was added. After stirring further for 30 minutes and filtering, the filtrate was distilled under reduced pressure. A compound represented by [Chemical Formula 2-1] was obtained by purifying the obtained compound by reverse-phase column chromatography (5.23 g, 43.3%).

$R_f$=0.45 (RP-18C, acetonitrile:distilled water=1:3 v/v).

Preparation Example

Preparation Example 2.1

Preparation of Compound of [Chemical Formula 3-1]

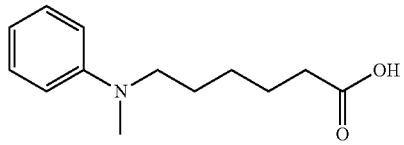 [SMILES: CN(CCCCCC(=O)O)c1ccccc1]

6.87 g of N-methylaniline (64 mmol, 1 eq) was stirred with 100 mL of 1,2-dichlorobenzene for 30 minutes. After adding 15 g of 6-bromohexanoic acid (77 mmol, 1.2 eq), the mixture was refluxed at 140° C. for 12 hours. Upon completion of reaction, 500 mL of hexane was added and the mixture was stirred for 10 minutes. After drying under reduced pressure, a compound of [Chemical Formula 3-1] was obtained by purifying by silica gel column chromatography (7.48 g, 52.8%).

$R_f$=0.49 (dichloromethane:hexane:methanol=10:1:1 v/v).
LC/MS: 221.1 (theoretical $C_{13}H_{19}NO_2$ 221.3).

Preparation Example 2.2

Preparation of Compound of [Chemical Formula 3-2]

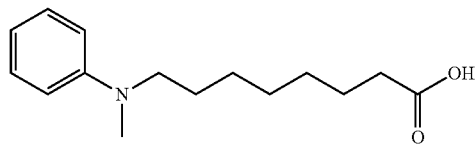 [SMILES: CN(CCCCCCCC(=O)O)c1ccccc1]

A compound of [Chemical Formula 3-2] was obtained in the same manner as in Preparation Example 2.1 except that 10 g of 8-bromooctanoic acid (45 mmol, 1 eq) was used instead of 15 g of 6-bromohexanoic acid (77 mmol, 1.2 eq) (3.55 g, 31.6%).

$R_f$=0.55 (dichloromethane:hexane:methanol=10:1:1 v/v).
LC/MS: 249.99 (theoretical $C_{15}H_{23}NO_2$ 249.35).

EXAMPLE

Example 1

Preparation of Compound of [Chemical Formula 6]

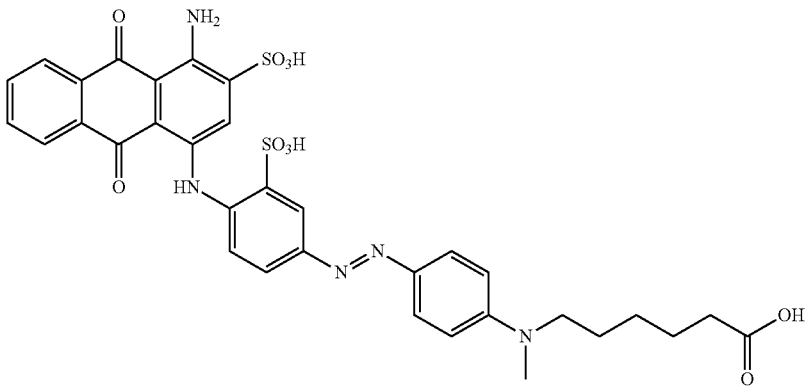 [SMILES: CN(CCCCCC(=O)O)c1ccc(/N=N/c2ccc(Nc3cc(S(=O)(=O)O)c(N)c4c3C(=O)c3ccccc3C4=O)c(S(=O)(=O)O)c2)cc1]

3 g of the compound prepared in Preparation Example 1 (6.13 mmol, 1 eq) was dissolved in a mixture of 100 mL of water and 50 mL of methanol. After cooling to 10° C. or below, 550 mg (7.97 mmol, 1.3 eq) of sodium nitrite dissolved in 5 mL of water was slowly added to the cooled solution. Then, after adding 6.4 mL of strong hydrochloric acid (61.3 mmol, 10 eq) and conducting reaction for 1 hour, 1.36 g of the compound prepared in Preparation Example 2.1 (6.13 mmol, 1 eq) dissolved in 50 mL of methanol was added. After stirring for 30 minutes, pH was adjusted to 6 by adding an aqueous sodium carbonate solution and the mixture was stirred until the next day. Upon completion of reaction, a compound of [Chemical Formula 6] was prepared by purifying a compound obtained by distillation under reduced pressure by reverse-phase column chromatography (853 mg, 19.3%).

$R_f$=0.45 (RP-18C, acetonitrile:distilled water=1:3 v/v).
LC/MS=719.6 (theoretical $C_{33}H_{29}N_5O_{10}S_2^{2-}$ 719.14).
$\lambda_{abs}$ (PBS): 481 nm, 626 nm.

Example 2

Preparation of Compound of [Chemical Formula 7]

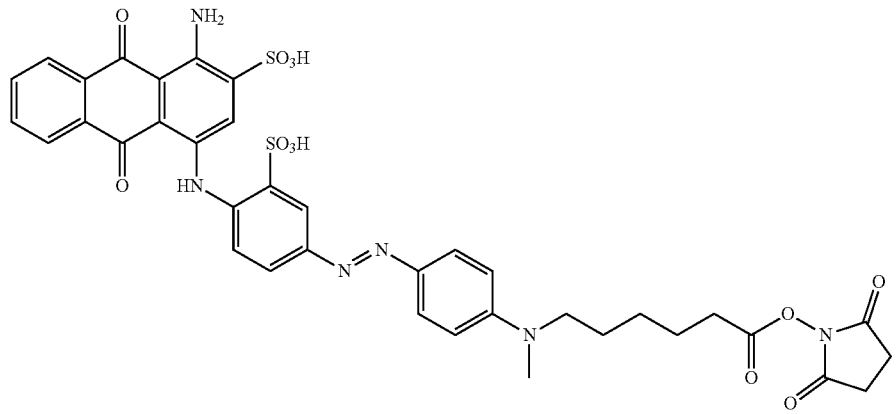 [SMILES: CN(CCCCCC(=O)ON1C(=O)CCC1=O)c1ccc(/N=N/c2ccc(Nc3cc(S(=O)(=O)O)c(N)c4c3C(=O)c3ccccc3C4=O)c(S(=O)(=O)O)c2)cc1]

400 mg of the compound prepared in Preparation Example 1 (0.55 mmol, 1 eq) was dissolved in 50 mL of DMF. After heating to 40° C., 0.96 mL. of N,N-diisopropylethylamine (5.54 mmol, 10 eq) was added. After adding 426 mg of N,N'-disuccinimidyl carbonate (1.66 mmol, 3 eq) dissolved in 1 mL of DMF, the reaction mixture was stirred for 1 hour. Upon completion of reaction, the target compound was prepared by filtering and drying precipitates formed by adding ethyl acetate.

Example 3

Preparation of Compound of [Chemical Formula 8]

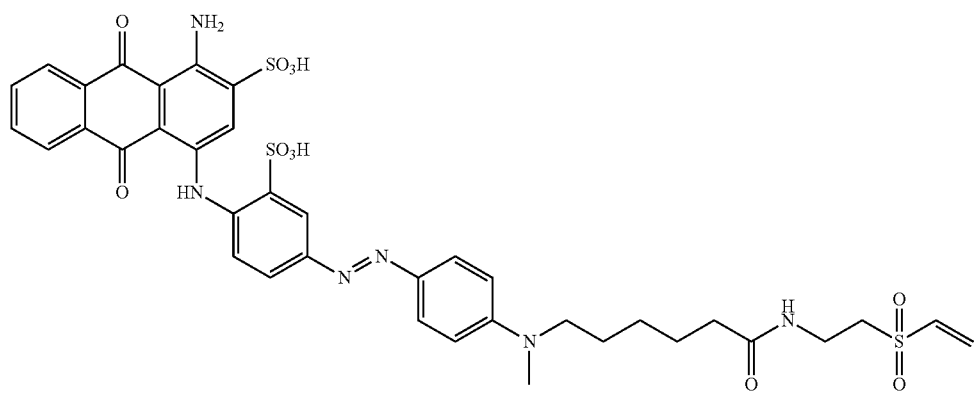 [SMILES: C=CS(=O)(=O)CCNC(=O)CCCCCN(C)c1ccc(/N=N/c2ccc(Nc3cc(S(=O)(=O)O)c(N)c4c3C(=O)c3ccccc3C4=O)c(S(=O)(=O)O)c2)cc1]

After dissolving the compound prepared in Example 2 in 40 mL of DMF and adding 0.96 mL of N,N-diisopropylethylamine and 115 mg of 2-(2'-chloroethylsulfony)ethylamine hydrochloride (0.55 mmol, 1 eq), the mixture was stirred at 40° C. (for 24 hours or longer). Upon completion of reaction, precipitates were formed by adding ethyl acetate to the reaction mixture. After filtering and drying the precipitates, the target compound was prepared by purifying by reverse-phase column chromatography (97 mg, 21.0%).

$R_f$=0.4 (RP-18C, acetonitrile:distilled water=1:4 v/v).

LC/MS=838.93 (theoretical $C_{37}H_{38}N_6O_{11}S_3$ 838.93).

$\lambda_{abs}$ (PBS): 481 nm, 626 nm.

Example 4

Preparation of Compound of [Chemical Formula 11]

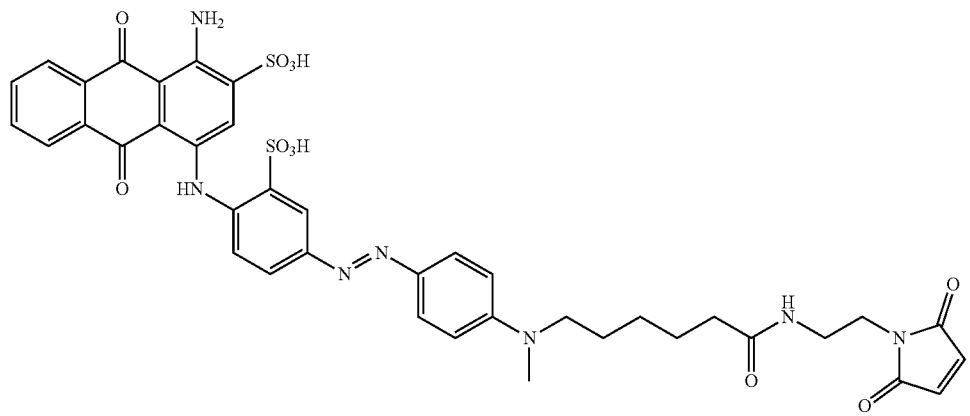 [SMILES: CN(CCCCCC(=O)NCCN1C(=O)C=CC1=O)c1ccc(/N=N/c2ccc(Nc3cc(S(=O)(=O)O)c(N)c4c3C(=O)c3ccccc3C4=O)c(S(=O)(=O)O)c2)cc1]

The target compound was prepared in the same manner as in Example 3 except that N-(2-aminoethyl)maleimide(N-(2-aminoethyl)maleimide) was used instead of 2-(2'-chloroethylsulfony)ethylamine hydrochloride.

$R_f$=0.45 (RP-C18, acetonitrile:distilled water=3:7 v/v).
LC/MS=841.5 (theoretical $C_{39}H_{35}N_7O_{11}S_2^{2-}$ 841.18).
$\lambda_{abs}$ (PBS): 481 nm, 626 nm.

Example 5

Preparation of Compound of [Chemical Formula 13]

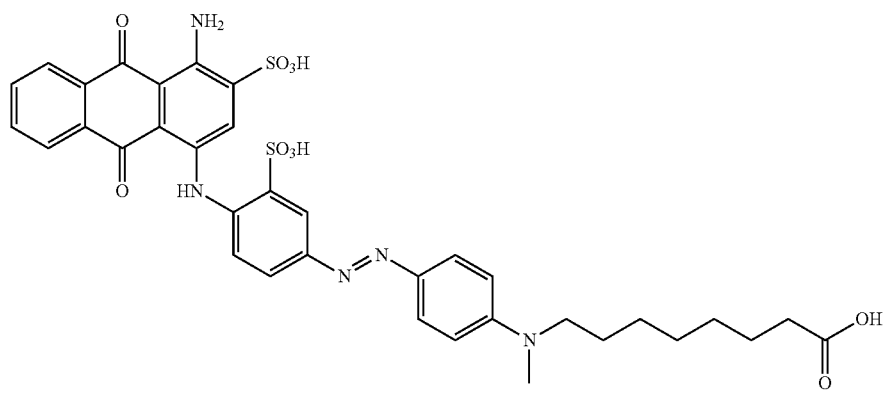 [SMILES: CN(CCCCCCCC(=O)O)c1ccc(/N=N/c2ccc(Nc3cc(S(=O)(=O)O)c(N)c4c3C(=O)c3ccccc3C4=O)c(S(=O)(=O)O)c2)cc1]

A compound of [Chemical Formula 13] was prepared in the same manner as in Example 1 except that the compound of Preparation Example 2.2 was used instead of the compound of Preparation Example 2.1 (570 mg, 14.9%).

$R_f$=0.25 (RP-18C, acetonitrile:distilled water=1:3 v/v).
LC/MS=747.7 (theoretical $C_{35}H_{33}N_5O_{10}S_2^{2-}$ 747.17).
$\lambda_{abs}$ (PBS): 472 nm, 624 nm.

Example 6

Preparation of Compound of [Chemical Formula 14]

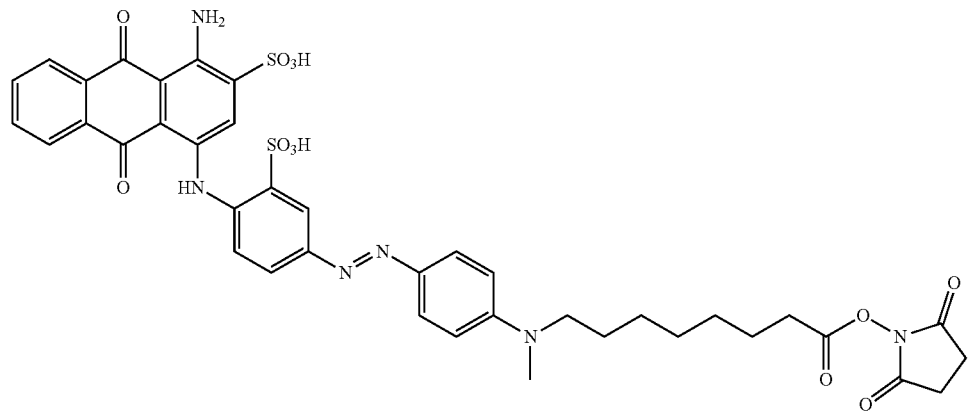 [SMILES: CN(CCCCCCCC(=O)ON1C(=O)CCC1=O)c1ccc(/N=N/c2ccc(Nc3cc(S(=O)(=O)O)c(N)c4c3C(=O)c3ccccc3C4=O)c(S(=O)(=O)O)c2)cc1]

The target compound was prepared in the same manner as in Example 2 except that the compound of Example 5 was used instead of the compound of Example 1.

Example 7

Preparation of Compound of [Chemical Formula 15]

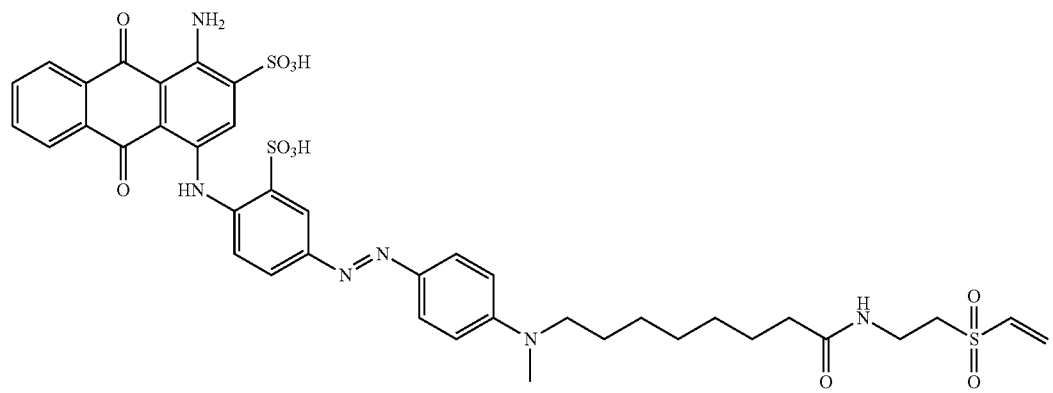 [SMILES: C=CS(=O)(=O)CCNC(=O)CCCCCCCN(C)c1ccc(/N=N/c2ccc(Nc3cc(S(=O)(=O)O)c(N)c4c3C(=O)c3ccccc3C4=O)c(S(=O)(=O)O)c2)cc1]

The target compound was prepared in the same manner as in Example 3 except that the compound of Example 6 was used instead of the compound of Example 2 (35 mg, 18.1%).

$R_f$=0.5 (RP-18C, acetonitrile:distilled water=1:2 v/v).

LC/MS=865.0 (theoretical $C_{39}H_{41}N_6O_{11}S^{3-}$ 865.20).

$\lambda_{abs}$ (PBS): 472 nm, 624 nm.

Example 8

Preparation of Compound of [Chemical Formula 16]

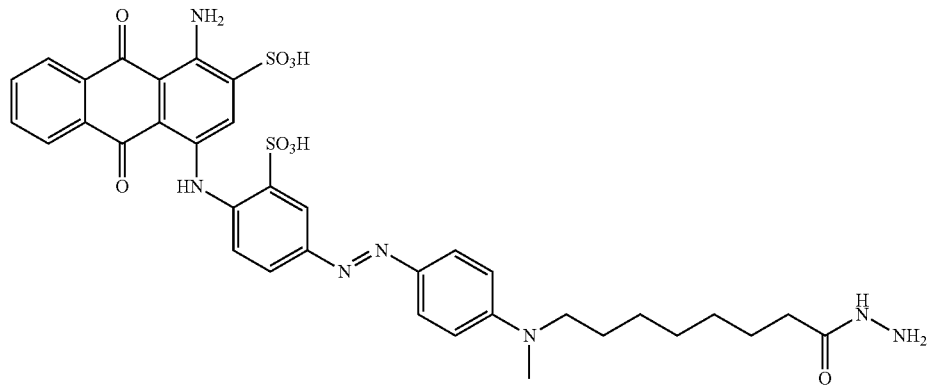 [SMILES: CN(CCCCCCCC(=O)NN)c1ccc(/N=N/c2ccc(Nc3cc(S(=O)(=O)O)c(N)c4c3C(=O)c3ccccc3C4=O)c(S(=O)(=O)O)c2)cc1]

The target compound was prepared in the same manner as in Example 3 except that the compound of Example 6 was used instead of the compound of Example 2 and tert-butyl carbazate was used instead of 2-(2'-chloroethylsulfony)ethylamine hydrochloride.

Example 9

Preparation of Compound of [Chemical Formula 17]

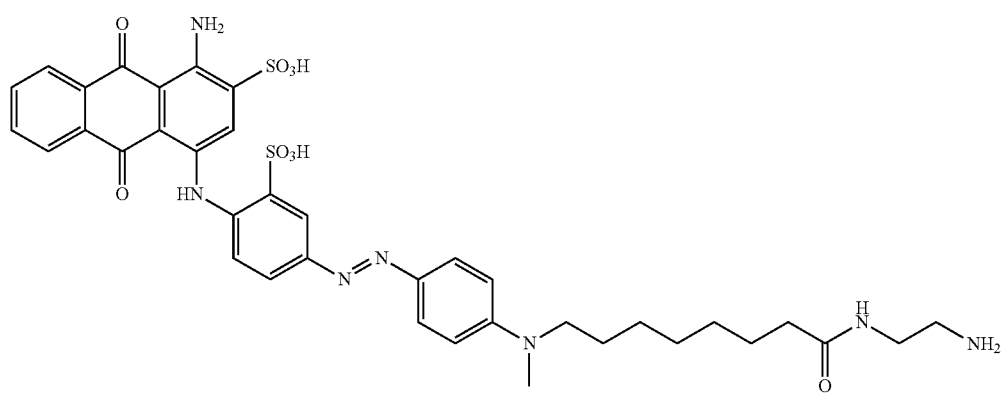 [SMILES: CN(CCCCCCCC(=O)NCCN)c1ccc(/N=N/c2ccc(Nc3cc(S(=O)(=O)O)c(N)c4c3C(=O)c3ccccc3C4=O)c(S(=O)(=O)O)c2)cc1]

The target compound was prepared in the same manner as in Example 3 except that the compound of Example 6 was used instead of the compound of Example 2 and ethylenediamine was used instead of 2-(2'-chloroethylsulfony)ethylamine hydrochloride.

Example 10

Preparation of Compound of [Chemical Formula 18]

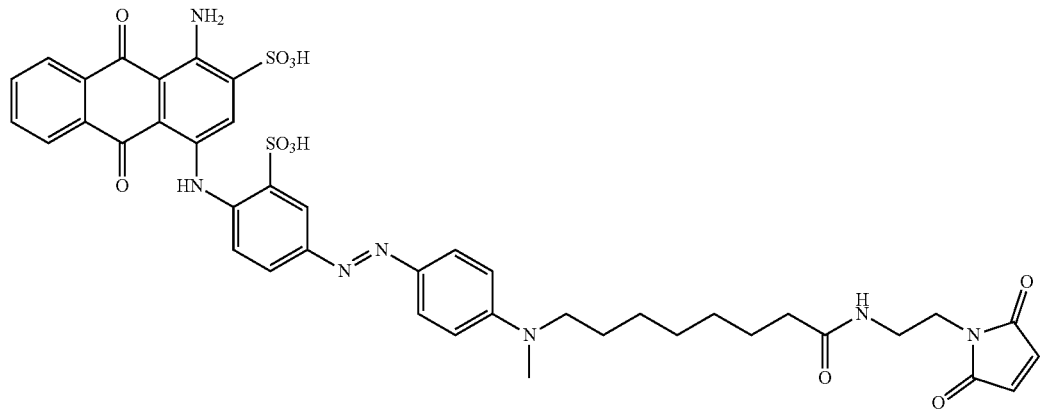 [SMILES: CN(CCCCCCCC(=O)NCCN1C(=O)C=CC1=O)c1ccc(/N=N/c2ccc(Nc3cc(S(=O)(=O)O)c(N)c4c3C(=O)c3ccccc3C4=O)c(S(=O)(=O)O)c2)cc1]

The target compound was prepared in the same manner as in Example 3 except that the compound of Example 6 was used instead of the compound of Example 2 and N-(2-aminoethyl)maleimide was used instead of 2-(2'-chloroethylsulfony)ethylamine hydrochloride.

Example 11

Preparation of Compound of [Chemical Formula 19]

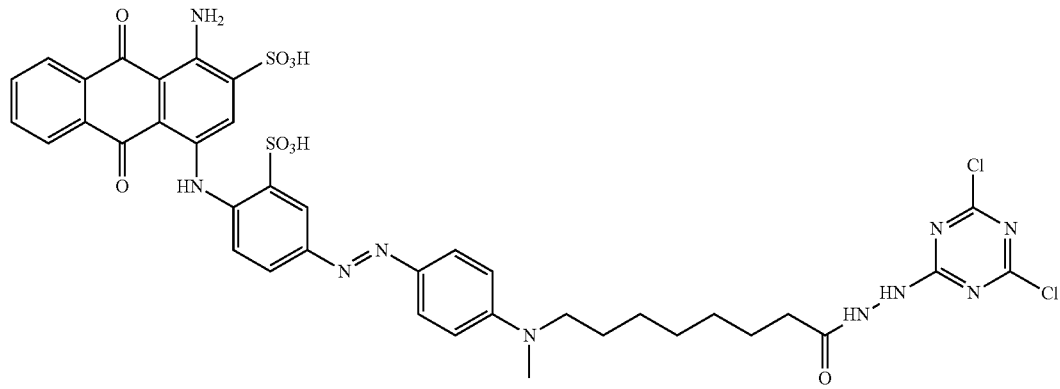 [SMILES: CN(CCCCCCCC(=O)NNc1nc(Cl)nc(Cl)n1)c1ccc(/N=N/c2ccc(Nc3cc(S(=O)(=O)O)c(N)c4c3C(=O)c3ccccc3C4=O)c(S(=O)(=O)O)c2)cc1]

The target compound was prepared in the same manner as in Example 3 except that the compound of Example 8 was used instead of the compound of Example 2 and cyanuric chloride was used instead of 2-(2'-chloroethylsulfony)ethylamine hydrochloride.

Test Example 1

Comparison of Absorption Spectra

In order to investigate the absorption intensity and spectrum of the anthraquinone compound according to the present disclosure, the absorption spectra of the compounds of Example 1 and Example 6 and commercially available BHQ-3 as a comparative example were compared. Stock solutions were prepared by dissolving the compounds of Example 1 and Example 6 according to the present disclosure in distilled water. BHQ-3 was dissolved in a small amount of DMSO according to the manufacturer's instructions and diluted with distilled water. The absorption spectra are shown in FIG. 1.

BHQ-3 was dissolved in DMSO and then diluted with water because it is not dissolved in water.

As seen from FIG. 1, compounds of Example 1 and Example 6 showed absorption spectra in a broader range of 300-800 nm than BHQ-3. Whereas BHQ-3 showed negative (−) absorption in the range of 750-800 nm, the compounds of Example 1 and Example 6 did not show negative absorption.

Figure 2:
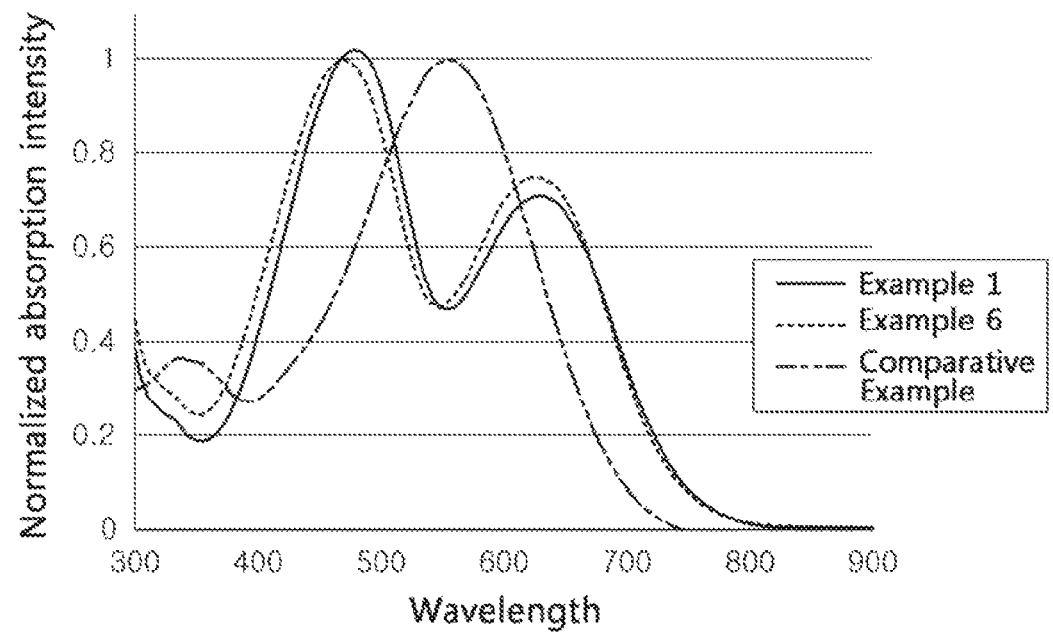
FIG. 2 shows the absorption spectra of compounds according to an exemplary embodiment of the present disclosure and a comparative example, normalized to the maximum absorption intensity.

FIG. 2 shows the absorption spectra of the compounds normalized to the maximum absorption intensity. Whereas the compounds of Example 1 and Example 6 showed absorption spectra in the range of 300-800 nm, the compound of the comparative example showed absorption spectra in the range of 300-750 nm. Accordingly, it can be seen that the anthraquinone compound according to the present disclosure shows absorption in a broader wavelength range. Also, it can be seen that the anthraquinone compound according to the present disclosure is effective in absorption of near-infrared fluorescence because it shows stronger absorption at the wavelength of 650 nm or higher.

Test Example 2

Measurement of Fluorescence Quenching Effect

As a known fluorophore-peptide-quencher combination, a fluorophore-peptide-quencher derivative (Cy5.5-peptide-BHQ-3) prepared by labeling the N-terminal of $NH_2$-GPL-GVRGKBB—COOH, which is a peptide substrate selectively cleaved by MMP-2 protease, with a near-infrared fluorescent dye such as Cy5.5 NHS ester and labeling the amine group of lysine with BHQ-3 was used. When MMP-2 protease is added to the derivative, the near-infrared fluorescence that has been quenched by the quenching dye is restored as the peptide is cleaved.

In order to investigate the quenching effect of the anthraquinone compound according to the present disclosure, (FNR-675)-peptide-(compound of [Chemical Formula 7]) was synthesized by labeling the peptide substrate with FNR-675 NHS ester (BioActs), which is a fluorescent dye that exhibits the same fluorescence as Cy5.5, and then binding the compound of Example 2.

Then, an enzymatic cleavage experiment was performed by adding MMP-2 protease to the (FNR-675)-peptide-(compound of [Chemical Formula 7]).

After mixing 50 μL of a TCNB buffer (0.1 M Tris, 5 mM calcium chloride, 200 mM NaCl, 0.1% Brij), 50 μL of MMP-2 protease and 1 μL of 100 mM p-aminophenylmercuric acid, 10 μL of the mixture was taken and diluted with 90 μL of a TCNB buffer. Then, the MMP-2 protease was activated by incubating at 37° C. for 1 hour. After dissolving the (FNR-675)-peptide-(compound of [Chemical Formula 7]) in a TCNB buffer to a concentration of 1 mg/2 mL, a peptide substrate solution was prepared by taking 40 μL of the mixture and diluting with 3,960 μL of a TNCB buffer. After adding the solution of the activated MMP-2 protease to the peptide substrate solution, restoration of fluorescence with time was measured while maintaining temperature at 37° C. The results shown in FIG. 3. The fluorescence intensity was measured at 675 nm (excitation) and 698 nm (fluorescence).

Figure 3:
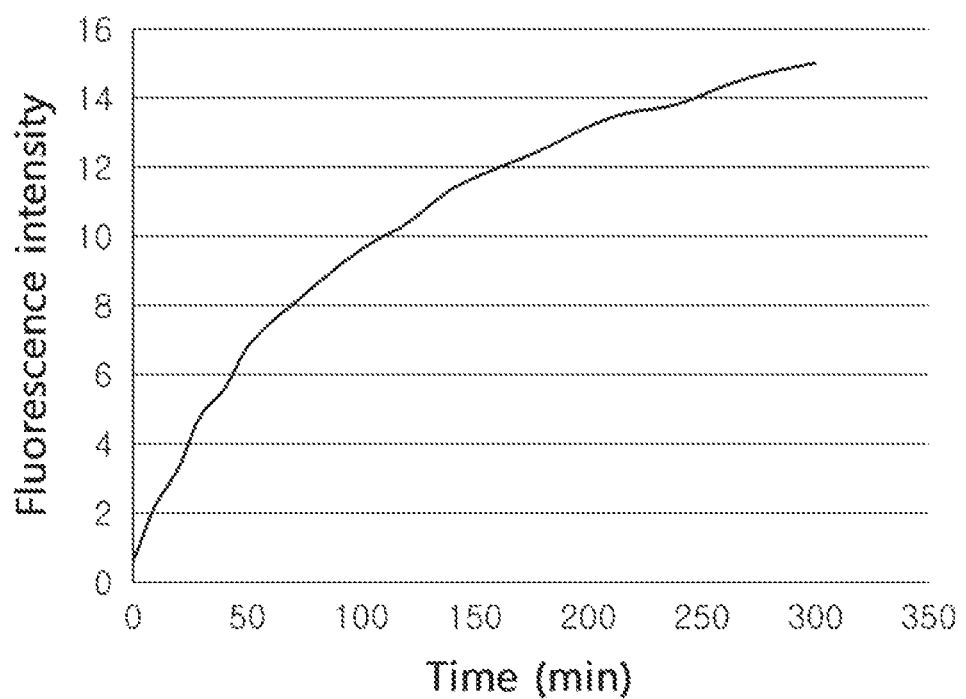
FIG. 3 shows a result of preparing a fluorophore-peptide-quencher combination using a compound according to the present disclosure prepared in Example 2 and measuring a fluorescence restoration effect through an enzymatic cleavage experiment.

From FIG. 3, it can be seen that the fluorescence was restored with time. 15 times or more was restored after 300 minutes.

Based on the results of Test Examples 1 and 2, it can be seen that the compound of [Chemical Formula 1] according to the present disclosure has superior ability of absorbing light in the visible and near-infrared wavelength regions and is expected to be effectively used to quench or restore the fluorescence of biomolecules.

INDUSTRIAL APPLICABILITY

When selecting a quenching dye for controlling or quenching the fluorescence of a fluorescent dye, it is of the most importance whether the absorption wavelength range of the quenching dye covers (overlaps with) the fluorescence wavelength range of the fluorescent dye. The anthraquinone compound according to the present disclosure has a broad and high absorption spectrum in the visible and near-infrared wavelength regions so as to cover the entire fluorescence wavelengths of commercially available visible and near-infrared dyes and also has high stability and superior solubility in aqueous conditions so that it can easily label a biomolecule manipulated in an aqueous buffer.

The invention claimed is:

1. An anthraquinone compound represented by [Chemical Formula 1]:

[Chemical Formula 1]

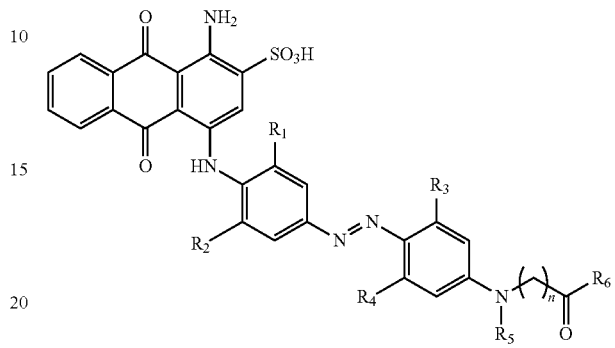

where each of $R_1$, $R_2$, $R_3$ and $R_4$, which are identical to or different from each other, is independently selected from hydrogen, a hydroxyl group, an amine group, a nitro group, a $C_1$-$C_6$ alkyl group, a $C_7$-$C_{10}$ alkyl group, a $C_1$-$C_6$ alkoxy group, a sulfonic acid group and a sulfonate group, $R_5$ is selected from a $C_1$-$C_6$ alkyl group and a $C_7$-$C_{10}$ alkyl group, $R_6$ is selected from a hydroxyl group, a hydrazinyl group, $NH(CH_2)_p NH_2$, a N-hydroxysuccinimide group, NH—$(CH_2)_q$—$N(CO)_2C_2H_2$, a 2,4-dihalo-6-hydrazino-1,3,5-triazine group and NH—A—$SO_2CH=CH_2$, A is selected from $(CH_2)_m$, para-$(C_6H_4)$ and meta-$(C_6H_4)$, each of m, p and q, which are identical to or different from each other, is independently an integer from 1 to 10, and n is an integer from 1 to 23.

2. The anthraquinone compound according to claim 1, wherein [Chemical Formula 1] is [Chemical Formula 4] or [Chemical Formula 5]:

[Chemical Formula 4]

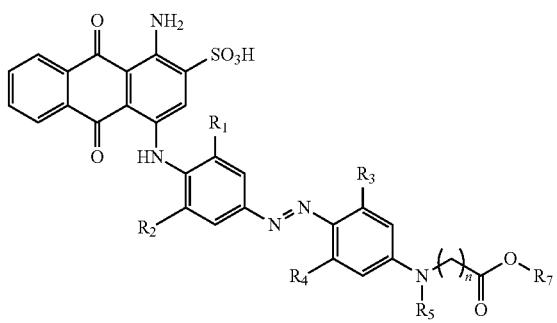

-continued

[Chemical Formula 5]

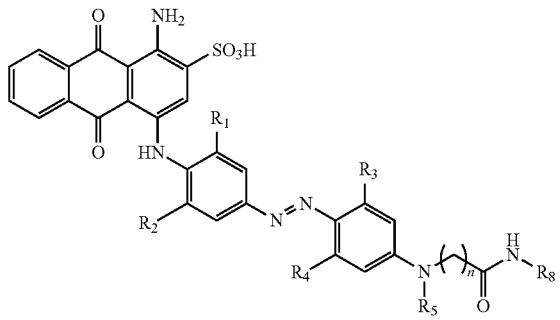

wherein
each of $R_1$, $R_2$, $R_3$ and $R_4$, which are identical to or different from each other, is independently selected from hydrogen, a hydroxyl group, an amine group, a nitro group, a $C_1$-$C_6$ alkyl group, a $C_7$-$C_{10}$ alkyl group, a $C_1$-$C_6$ alkoxy group, a sulfonic acid group and a sulfonate group, $R_5$ is selected from a $C_1$-$C_6$ alkyl group and a $C_7$-$C_{10}$ alkyl group, $R_7$ is hydrogen or a succinimide group, $R_8$ is selected from an amine group, a $C_1$-$C_{10}$ alkylamine group, a $C_1$-$C_{10}$ alkylmaleimidyl group, a 2,4-dihalo-6-amino-1,3,5-triazine group and A—$SO_2CH$=$CH_2$, A is selected from $(CH_2)_m$, para-$(C_6H_4)$ and meta-$(C_6H_4)$, m is an integer from 1 to 10, and n is an integer from 1 to 23.

3. The anthraquinone compound according to claim 1, wherein [Chemical Formula 1] is selected from a group consisting of [Chemical Formula 6] through [Chemical Formula 19]:

[Chemical Formula 6]

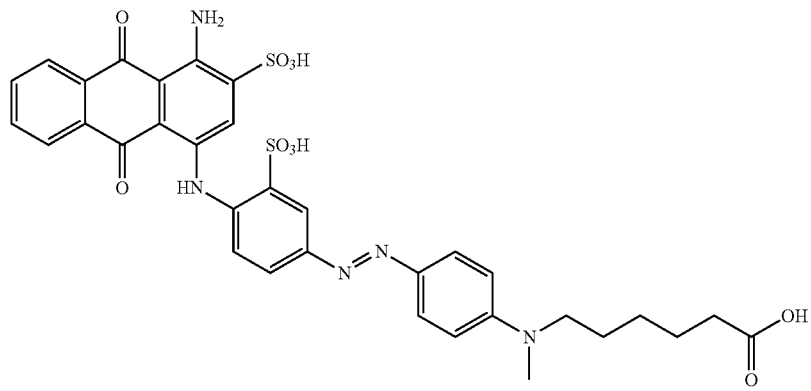

[Chemical Formula 7]

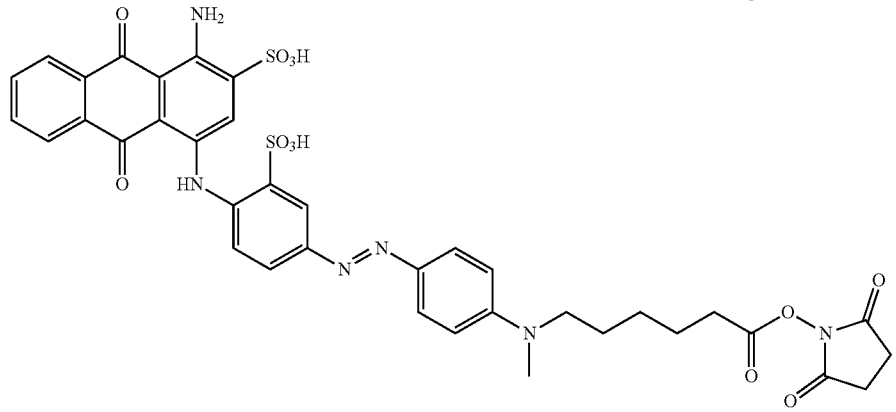

[Chemical Formula 8]

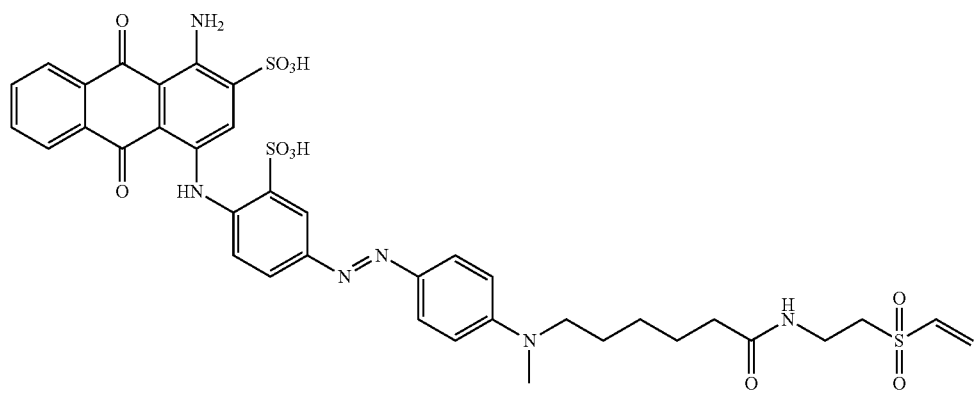

[Chemical Formula 9]
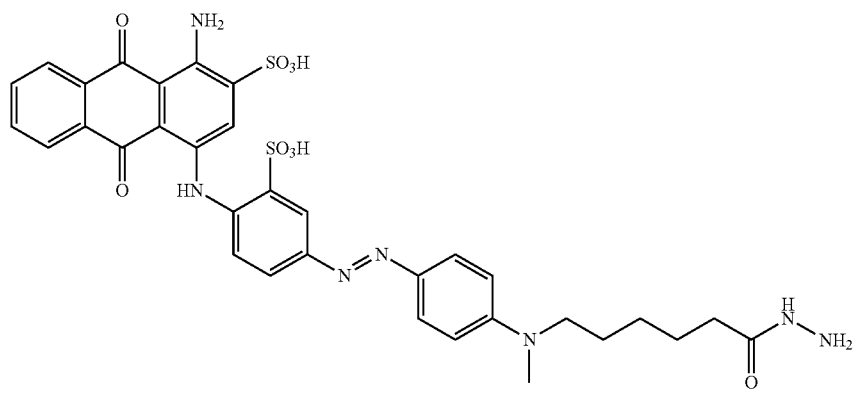
[Chemical Formula 10]
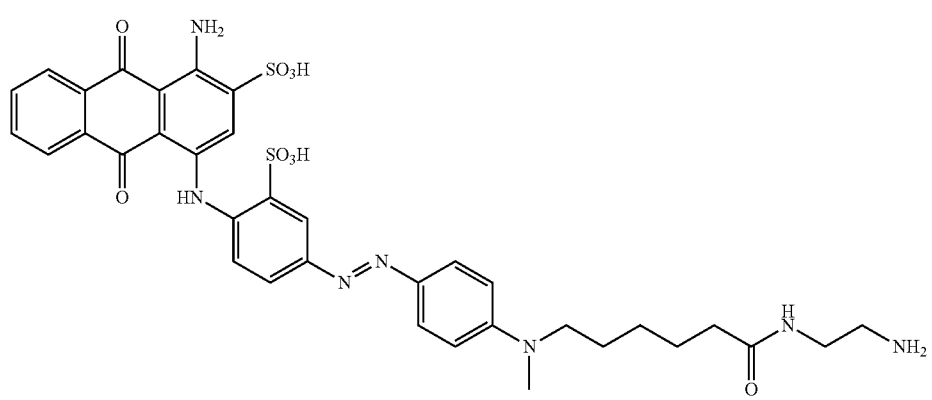
[Chemical Formula 11]
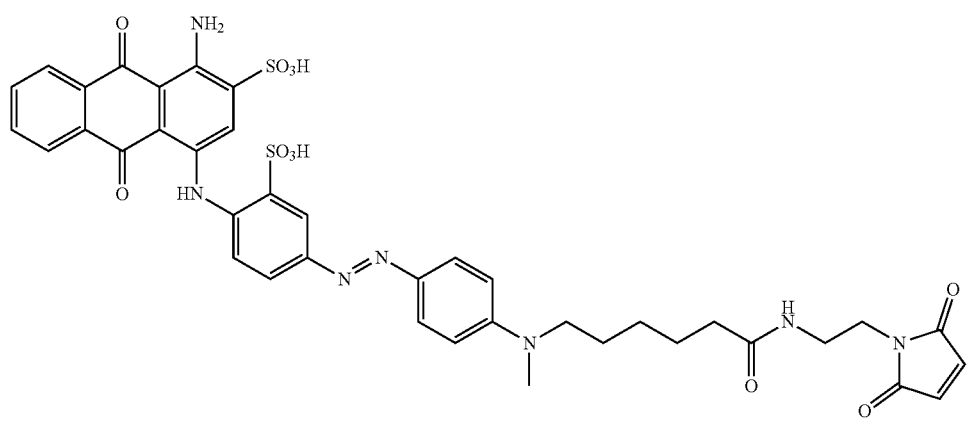
[Chemical Formula 12]
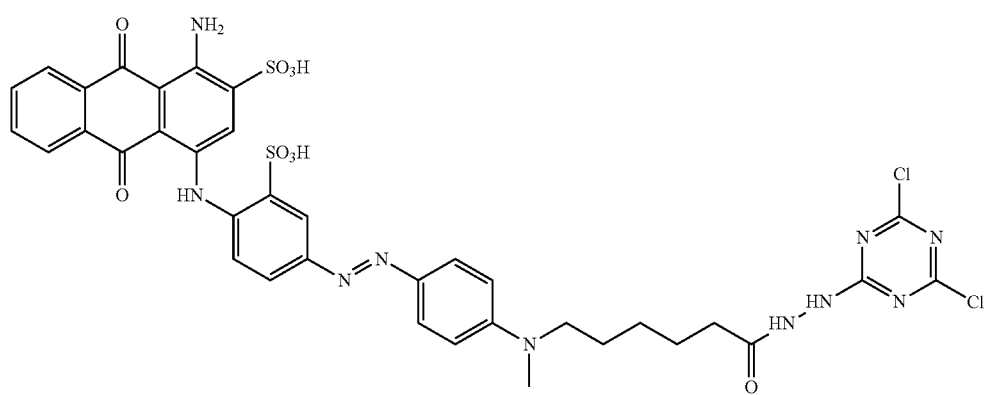

[Chemical Formul 13]
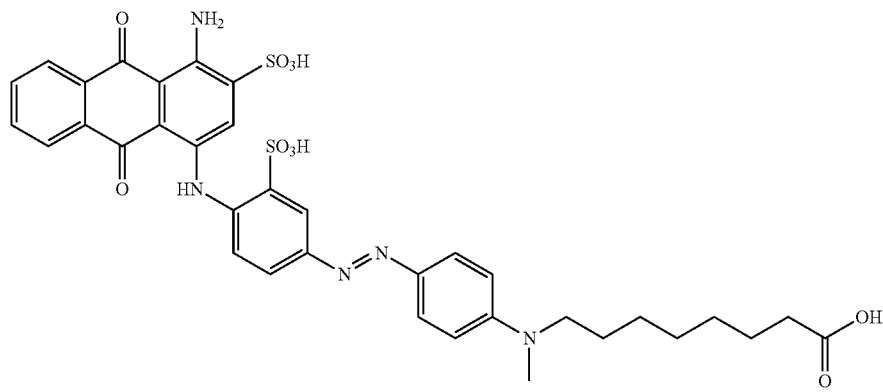
[Chemical Formula 14]
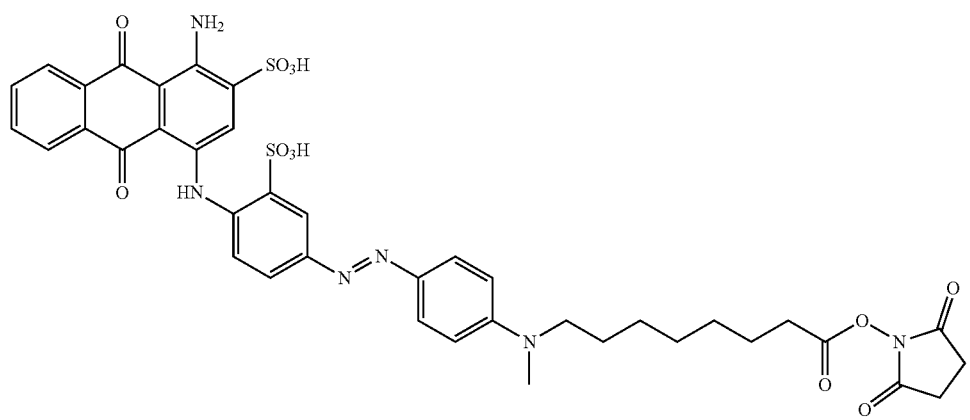
[Chemical Formula 15]
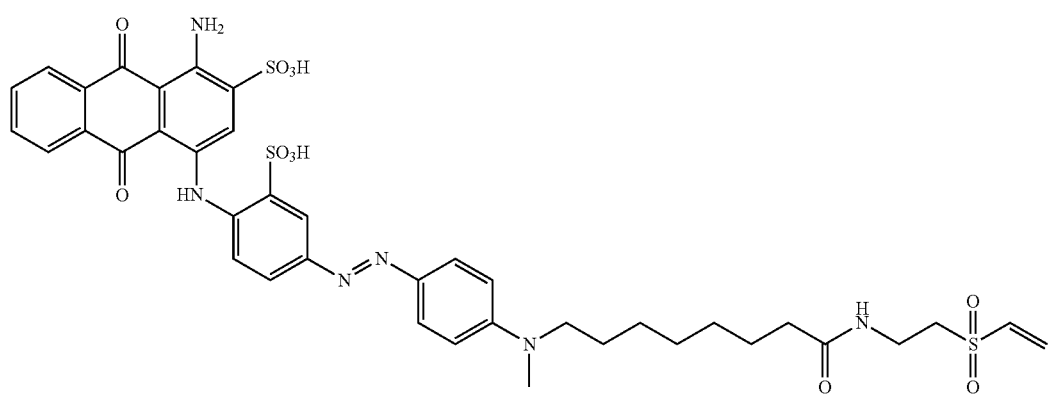
[Chemical Formula 16]
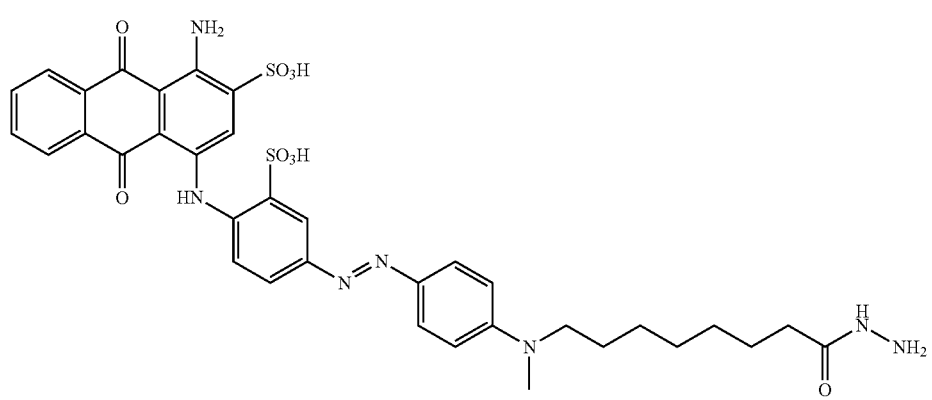

[Chemical Formula 17]

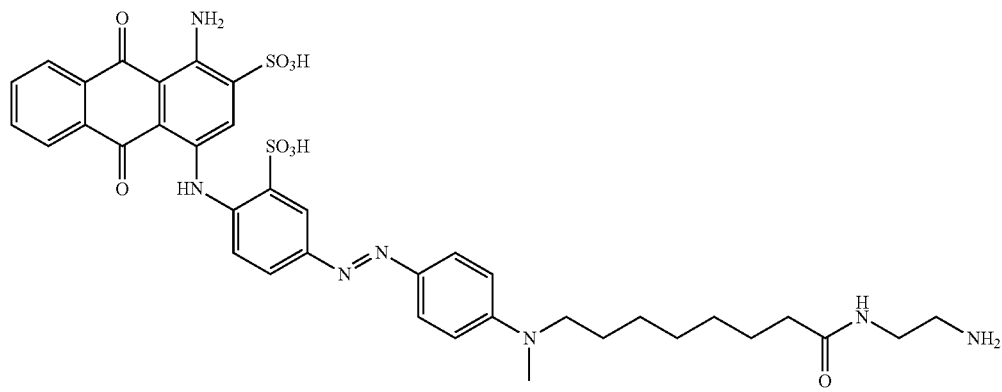

[Chemical Formula 18]

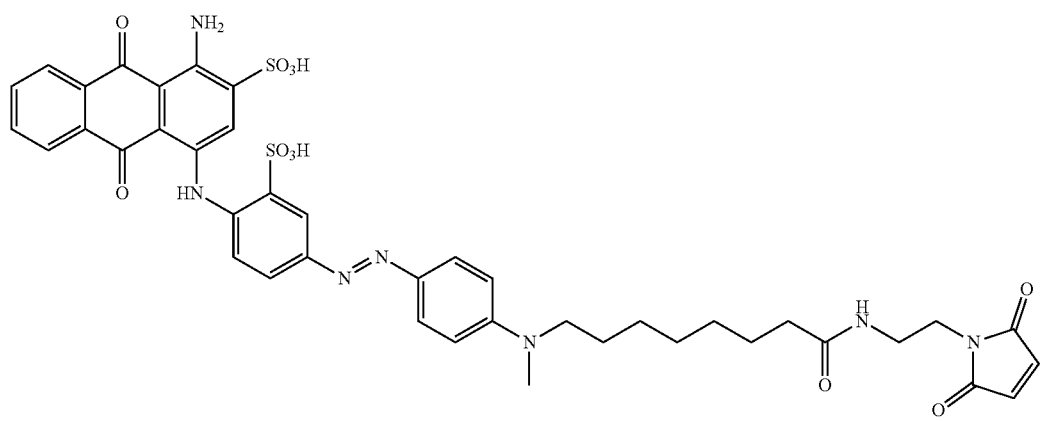

[Chemical Formula 19]

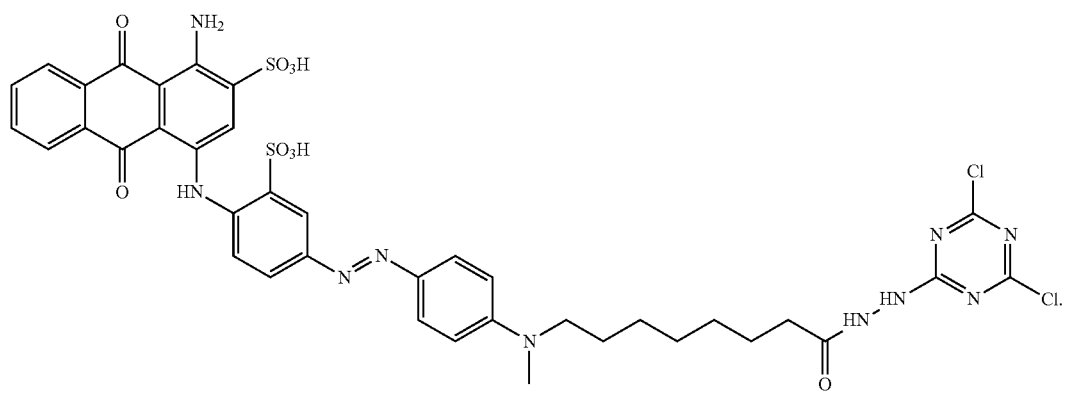

4. The anthraquinone compound according to claim 1, which absorbs light with a wavelength of 300-900 nm.

5. The anthraquinone compound according to claim 1, which labels a biomolecule comprising an amine group, a hydroxyl group or a thio group.

6. The anthraquinone compound according to claim 5, wherein the biomolecule is one or more selected from a group consisting of a protein, a peptide, a carbohydrate, a sugar, a fat, an antibody, a proteoglycan, a glycoprotein and a siRNA.

7. A method for preparing an anthraquinone compound represented by [Chemical Formula 1], comprising:
  preparing a compound of [Chemical Formula 2] into a diazonium salt; and
  obtaining a compound of [Chemical Formula 1] by reacting the diazonium salt with a compound of [Chemical Formula 3]:

[Chemical Formula 2]

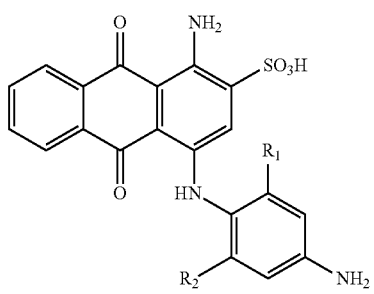

-continued

[Chemical Formula 3]

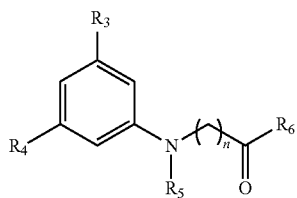

[Chemical Formula 1]

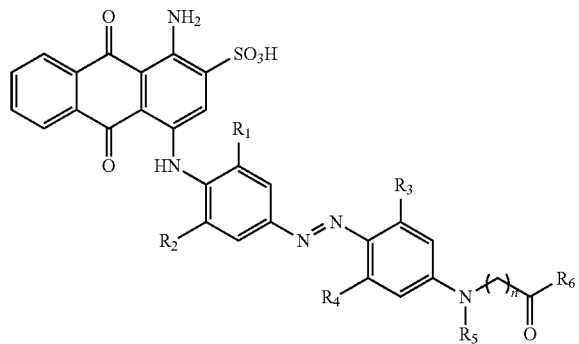

wherein
each of $R_1$, $R_2$, $R_3$ and $R_4$, which are identical to or different from each other, is independently selected from hydrogen, a hydroxyl group, an amine group, a nitro group, a $C_1$-$C_6$ alkyl group, a $C_7$-$C_{10}$ alkyl group, a $C_1$-$C_6$ alkoxy group, a sulfonic acid group and a sulfonate group, $R_5$ is selected from a $C_1$-$C_6$ alkyl group and a $C_7$-$C_{10}$ alkyl group,
$R_6$ is selected from a hydroxyl group, a hydrazinyl group, $NH(CH_2)_pNH_2$, a N-hydroxysuccinimide group, NH—$(CH_2)_q$—$N(CO)_2C_2H_2$, a 2,4-dihalo-6-hydrazino-1,3,5-triazine group and NH—A—$SO_2CH=CH_2$,
A is selected from $(CH_2)_m$, para-$(C_6H_4)$ and meta-$(C_6H_4)$,
each of m, p and q, which are identical to or different from each other, is independently an integer from 1 to 10, and
n is an integer from 1 to 23.

8. A quenching dye composition containing the anthraquinone compound according to claim 1 as an active ingredient.

9. The quenching dye composition according to claim 8, which absorbs light with a wavelength of 300-900 nm.

10. A method for labeling a biomolecule, comprising binding the anthraquinone compound according to claim 1 to a biomolecule,
wherein the biomolecule comprises at least one functional group selected from an amine group, a hydroxyl group and a thiol group, and the anthraquinone compound according to claim 1 is bound to the functional group.

11. The method according to claim 10, wherein the biomolecule is one or more selected from a group consisting of a protein, a peptide, a carbohydrate, a sugar, a fat, an antibody, a proteoglycan, a glycoprotein and a siRNA.

12. The method according to claim 10, wherein the anthraquinone compound according to claim 1 is labeled on a biomolecule and absorbs light with a wavelength of 300-900 nm.

* * * * *